US011273009B2

(12) United States Patent
Wilson et al.

(10) Patent No.: US 11,273,009 B2
(45) Date of Patent: Mar. 15, 2022

(54) SYSTEMS AND METHODS FOR TRIMMING DENTAL ALIGNERS

(71) Applicant: SDC U.S. SmilePay SPV, Nashville, TN (US)

(72) Inventors: Cherie Wilson, Nashville, TN (US); Josh Long, Nashville, TN (US); John Dargis, Nashville, TN (US); Tony Solarek, Nashville, TN (US)

(73) Assignee: SDC U.S. SmilePay SPV, Nashville, TN (US)

( * ) Notice: Subject to any disclaimer, the term of this patent is extended or adjusted under 35 U.S.C. 154(b) by 0 days.

(21) Appl. No.: 17/181,929

(22) Filed: Feb. 22, 2021

(65) Prior Publication Data

US 2021/0196430 A1    Jul. 1, 2021

Related U.S. Application Data

(63) Continuation-in-part of application No. 16/292,779, filed on Mar. 5, 2019, now Pat. No. 10,925,691.

(51) Int. Cl.
*A61C 7/00*       (2006.01)
*A61C 7/08*       (2006.01)
(Continued)

(52) U.S. Cl.
CPC ............. *A61C 7/002* (2013.01); *A61C 7/08* (2013.01); *G06F 30/30* (2020.01); *G06T 7/0012* (2013.01); *G06T 7/12* (2017.01); *G06T 17/00* (2013.01)

(58) Field of Classification Search
CPC ......... A61C 7/002; A61C 7/08; G06T 7/0012; G06T 7/12; G06T 17/00; G06T 19/00;
(Continued)

(56) References Cited

U.S. PATENT DOCUMENTS 8,684,729 B2   4/2014  Wen
9,943,386 B2   4/2018  Webber et al.
(Continued)

FOREIGN PATENT DOCUMENTS

WO    WO-2018/174843 A1    9/2018

OTHER PUBLICATIONS

Lin et al., "3D CAD for Design of Invisible Tooth Aligner", Proceedings of the 2005 IEEE International Conference on Mechatronics, Jul. 10-12, 2005, pp. 647-651 (Year: 2005).*
(Continued)

*Primary Examiner* — Nay A Maung
*Assistant Examiner* — Jose M Torres
(74) *Attorney, Agent, or Firm* — Foley & Lardner LLP

(57) ABSTRACT

Systems and methods for trimming dental aligners include a cut line system for identifying a first point and a second point based on a line around tooth (LAT) for a tooth of a model representative of a dentition of a user, where the first point is disposed on a tooth-gingiva interface of the tooth. The cut line system defines a cut plane at a distance from the first point toward the second point, where the cut plane intersects a line between the first point and the second point, identifies a plurality of points on the LAT based on the cut plane, defines a cut line based on the plurality of points on the LAT and the first point, and controls a cutting system to cut the dental aligner along the cut line.

18 Claims, 13 Drawing Sheets

(51) Int. Cl.
*G06T 17/00* (2006.01)
*G06F 30/30* (2020.01)
*G06T 7/00* (2017.01)
*G06T 7/12* (2017.01)

(58) Field of Classification Search
CPC ....... G06T 2207/30036; G06T 2210/41; G06T 2219/008; G06F 30/30; A61B 5/0064; A61B 5/0088; A61B 5/4547
See application file for complete search history.

(56) References Cited

U.S. PATENT DOCUMENTS

| | | | |
|---|---|---|---|
| 10,011,050 | B2 | 7/2018 | Kitching et al. |
| 10,098,709 | B1 | 10/2018 | Kitching et al. |
| 10,258,439 | B1 | 4/2019 | Kitching et al. |
| 10,466,676 | B1 * | 11/2019 | Do ................ G05B 19/402 |
| 10,945,812 | B1 * | 3/2021 | Raslambekov ......... G06T 17/20 |
| 2002/0177108 | A1 | 11/2002 | Pavlovskaia et al. |
| 2006/0003292 | A1 | 1/2006 | Lauren et al. |
| 2006/0199153 | A1 | 9/2006 | Liu et al. |
| 2008/0141534 | A1 | 6/2008 | Hilliard |
| 2008/0187887 | A1 | 8/2008 | Lu et al. |
| 2008/0254402 | A1 | 10/2008 | Hilliard |
| 2008/0305454 | A1 | 12/2008 | Kitching et al. |
| 2008/0306724 | A1 | 12/2008 | Kitching et al. |
| 2009/0113714 | A1 | 5/2009 | Greenberg |
| 2010/0173266 | A1 | 7/2010 | Lu et al. |
| 2013/0073071 | A1 | 3/2013 | Culp |
| 2013/0122448 | A1 | 5/2013 | Kitching |
| 2013/0144422 | A1 | 6/2013 | Choi et al. |
| 2014/0277665 | A1 | 9/2014 | Fisker |
| 2014/0315153 | A1 | 10/2014 | Kitching et al. |
| 2015/0132707 | A1 | 5/2015 | Huang et al. |
| 2016/0074138 | A1 | 3/2016 | Kitching et al. |
| 2017/0100214 | A1 | 4/2017 | Wen |
| 2017/0304023 | A1 | 10/2017 | Tsai et al. |
| 2018/0092714 | A1 | 4/2018 | Kitching et al. |
| 2018/0116762 | A1 | 5/2018 | Kopelman |
| 2018/0165818 | A1 | 6/2018 | Tsai et al. |
| 2018/0177570 | A1 | 6/2018 | Alauddin et al. |
| 2018/0304497 | A1 | 10/2018 | Kitching et al. |
| 2018/0333226 | A1 | 11/2018 | Tsai et al. |
| 2019/0008612 | A1 | 1/2019 | Kitching et al. |
| 2019/0102880 | A1 | 4/2019 | Parpara et al. |
| 2019/0167384 | A1 | 6/2019 | Borovinskih et al. |
| 2020/0015937 | A1 | 1/2020 | Stewart |
| 2020/0281689 | A1 | 9/2020 | Yancey et al. |
| 2021/0196430 | A1 | 7/2021 | Wilson et al. |

OTHER PUBLICATIONS

Lin et al., "Integration of 3D CAD, Reverse Engineering and Rapid Prototyping in Fabrication of Invisible Tooth Aligner", 2005 IEEE International Conference on Systems, Man and Cybernetics, Oct. 12-12, 2005, pp. 2431-2436 (Year: 2005).*

"Invisalign Manufacturing Process English" video, uploaded to YouTube on Apr. 7, 2014, https://www.youtube.com/watch?v=vsRO_wTR2a8, 125 pages of screenshots.

International Search Report and Written Opinion for International Application No. PCT/US2020/020728, dated Jun. 8, 2020, 6 pages.

International Search Report and Written Opinion for International Application No. PCT/US2020/027044, dated Jul. 16, 2020, 8 pages.

Somers, Jamie, "Tech tip: Undesirable undercuts", The Clearcorrect Blog, http://blog.clearcorrect.com/category/tech-tips.aspx?page=10, Oct. 16, 2015, 12 pages.

Wise, John, "Keeping the 'special' in the orthodontic specialty: part 1", Orthodontic Practice US, https://orthopracticeus.com/keeping-special-orthodontic-specialty-part-1, 2017, 10 pages.

* cited by examiner

US 11,273,009 B2

SYSTEMS AND METHODS FOR TRIMMING DENTAL ALIGNERS

CROSS-REFERENCE TO RELATED PATENT APPLICATIONS

This application is a continuation-in-part of U.S. patent application Ser. No. 16/292,779, filed Mar. 5, 2019, the contents of which are incorporated herein by reference in its entirety.

BACKGROUND

The present disclosure relates generally to intraoral devices. More specifically, the present disclosure relates to trimming or cutting dental aligners and other intraoral devices.

Dental aligners may be worn by a patient receiving orthodontic treatment. Some dental aligners may be fabricated by thermoforming aligner material to a dental mold. After thermoforming the aligner material to a dental mold, the formed aligner is cut and removed from the dental mold so that the aligner can be worn by the patient.

SUMMARY

At least one embodiment relates to a method of cutting a dental aligner. The method includes identifying a first point and a second point based on a line around tooth (LAT) for a tooth of a model representative of a dentition of a user. The first point is disposed on a tooth-gingiva interface of the tooth. The method further includes defining a cut plane at a distance from the first point toward the second point, where the cut plane intersects a line between the first point and the second point, identifying a plurality of points on the LAT based on the cut plane, defining a cut line based on the plurality of points on the LAT and the first point, and controlling a cutting system to cut the dental aligner along the cut line.

Another embodiment relates to a system for cutting a dental aligner. The system includes a cut line system and a cutting system. The cut line system is configured to identify a first point and a second point based on a line around tooth (LAT) for a tooth of a model representative of a dentition of a user. The first point is disposed on a tooth-gingiva interface of the tooth. The cut line system is further configured to define a cut plane at a distance from the first point toward the second point, where the cut plane intersects a line between the first point and the second point, identify a plurality of points on the LAT based on the cut plane, and define a cut line based on the plurality of points on the LAT and the first point. The cutting system includes a cutting tool configured to cut the dental aligner along the cut line.

Another embodiment relates to a non-transitory computer readable medium storing instructions that, when executed by a processor, cause the processor to perform operations. The operations include identifying a first point and a second point based on a line around tooth (LAT) for a tooth of a model representative of a dentition of a user, defining a cut plane at a distance from the first point toward the second point, where the cut plane intersects a line between the first point and the second point, identifying a plurality of points on the LAT based on the cut plane, and defining a cut line for cutting a dental aligner based on the plurality of points on the LAT and the first point.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the figures, described herein are systems and methods for trimming intraoral devices, such as dental aligners. A model analyzer is configured to receive a model representing a three-dimensional impression of a user's dentition which is used for forming an intraoral device, such as a dental aligner. A gingival line extractor is configured to identify a gingival line. The gingival line is defined by a juncture between the tooth and a gum. A cut line determiner selects points in the gingiva within the model for defining a cut line. When a plurality of points for the cut line are selected, the cut line determiner defines the cut line by joining the plurality of points. A cutting system controller controls a cutting tool of a cutting system to cut the intraoral device along the cut line to prepare the intraoral device for use. While the present disclosure primarily refers to the fabrication of dental aligners, it is noted that the present disclosure is not limited to fabricating only dental aligners. Rather, the present disclosure may be applied to fabricating other intraoral devices such as, but not limited to, mouth guards, retainers, expansion aligners, or other intraoral devices that are cut from a mold. Accordingly, it will be appreciated that any system or process disclosed herein can also be used to fabricate intraoral devices other than dental aligners.

Figure 1:
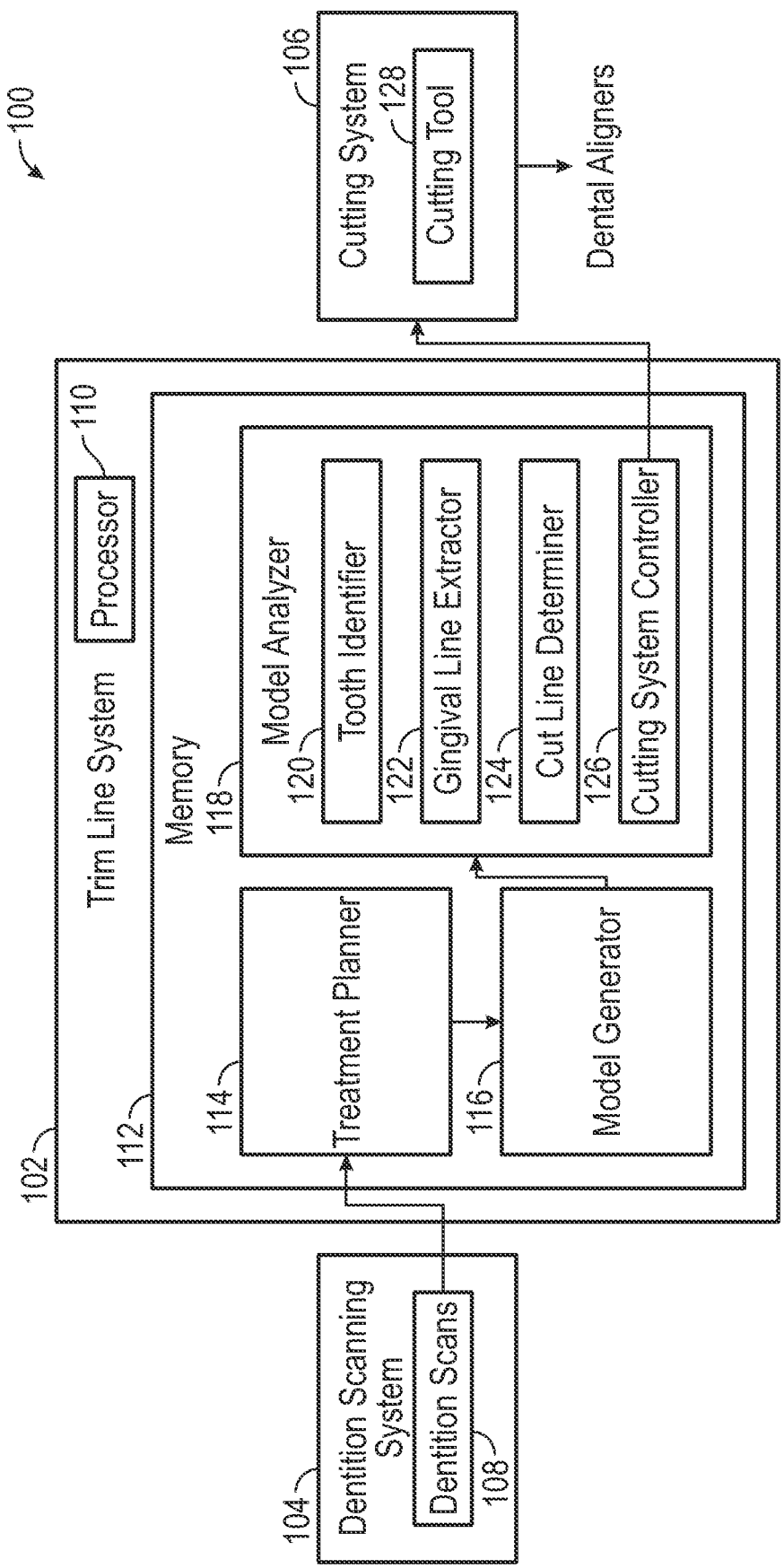
FIG. 1 is a block diagram showing a system for generating dental aligners, according to an illustrative embodiment.
Figure 14:
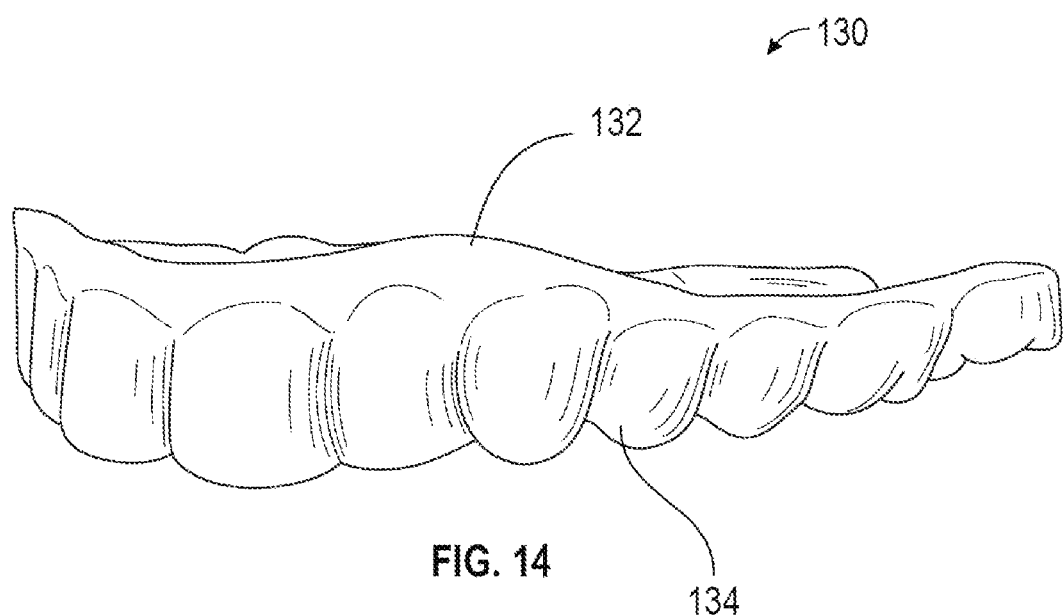
FIG. 14 is an illustration of a dental aligner fabricated using the system for generating dental aligners of FIG. 1, according to an illustrative embodiment.

Referring now to FIG. 1, an embodiment of a system 100 for fabricating dental aligners is shown. The system 100 is shown to include a cut line system 102, a dentition scanning system 104, and a cutting system 106. The dentition scanning system 104 includes any device, component, or group of devices or components configured to generate dentition scans 108. The dentition scans 108 may be digital scans of a physical dental impression (e.g., captured by a dental technician, a dentist, a user of a dental aligner). The dentition scans 108 may be direct scans of a patient's dentition. Hence, the dentition scans 108 may be direct scans of a patient's dentition captured by scanning the patient's dentition with a three-dimensional camera, or the dentition scans 108 may be indirect scans of the patient's dentition captured by scanning a physical model or impression of the patient's dentition. In either embodiment, the dentition scans 108 are three-dimensional representations of a patient's dentition. The dentition scans 108 may be used for fabricating a dental aligner, such as the dental aligner 130 shown in FIG. 14, as described in greater detail below.

In some implementations, the cut line system 102 may be embodied as or include a processing circuit which includes a processor 110 and memory 112. The processor 110 may be a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. The processor 110 also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function.

The memory 112 (e.g., memory, memory unit, storage device) may include one or more devices (e.g., RAM, ROM, EPROM, EEPROM, optical disk storage, magnetic disk storage or other magnetic storage devices, flash memory, hard disk storage, or any other medium) for storing data and/or computer code for completing or facilitating the various processes, layers and circuits described in the present disclosure. The memory 112 may be or include volatile memory or non-volatile memory, and may include database components, object code components, script components, or any other type of information structure for supporting the various activities and information structures described in the present disclosure. According to an illustrative embodiment, the memory 112 is communicably connected to the processor 110 via a processing circuit and includes computer code for executing (e.g., by the processing circuit or the processor 110) the processes described herein.

The memory 112 may store various modules or be comprised of a system of circuits. The circuits may include hardware, memory, and/or other components configured or implemented to execute various functions. The memory 112 may store a treatment planner 114, a model generator 116, and a model analyzer 118. The treatment planner 114 may be a circuit designed or implemented to perform various functions corresponding to generating a treatment plan for the user's dentition (e.g., based on the dentition scans 108). The model generator 116 may be configured to generate a model based on the generated treatment plan. The model may be a three-dimensional representation of the user's dentition at various intervals (e.g., at the start of the treatment plan and at various intervals throughout the treatment plan). The model analyzer 118 may be configured to analyze the models generated via the model generator 116 for fabricating dental aligners 130.

In various embodiments, the treatment planner 114 is configured to produce, generate, assemble, compile, or otherwise create a treatment plan for moving various teeth of a user's dentition. The treatment plan may be a series of movements for teeth of a user's dentition from a starting arrangement to an ending arrangement. The treatment plan may be generated by or through use of the treatment planner 114. In some embodiments, a dental technician or professional uses the treatment planner 114 to generate the treatment plan by manipulating individual teeth or groups of teeth shown in models based on the dentition scans 108. For instance, the treatment planner 114 may present models based on the dentition scans 108 from the dentition scanning system 104 to the dental professional, who then can manipulate various teeth within the dentition scans 108.

The treatment planner 114 is configured to generate various stages of the treatment plan to move the teeth from the starting position (e.g., their current position as represented within the dentition scan 108) to a final position selected or provided by the dental professional. In some embodiments, the treatment planner 114 is configured to create the treatment plan without the assistance of a dental professional. For instance, the treatment planner 114 may analyze the dentition scans 108 to align the teeth with a dental arch fitted to the teeth. The treatment planner 114 may then generate various stages of the treatment plan to move the teeth from the starting position to the final position.

The model generator 116 is configured to generate models of the user's dentition at the various stages of the treatment plan generated by or using the treatment planner 114. The model generator 116 generates a plurality of models including an initial model, a final model, and at least one intermediate model. The initial model corresponds to a first stage of the treatment plan. The final model corresponds to a final stage of the treatment plan. Each intermediate model corresponds to an intermediate stage of the treatment plan.

In various instances, the user is provided a dental aligner 130 to be worn at each stage of the treatment plan for a predetermined duration (e.g., one week, two weeks, one month). The dental aligners 130 are constructed from a material thermoformed to a physical model and worn in the user's mouth. The dental aligners 130 apply a force on at least one of the user's teeth to move at least one tooth according to the treatment plan.

In some embodiments, each stage of the treatment plan includes more than one dental aligner 130 having the same shape but having a different thickness or being constructed of a different material (e.g., a harder or softer material). For example, the treatment plan can specify that the user wears the softest dental aligner in a first sub-stage, followed by a dental aligner of medium hardness, followed by the hardest dental aligner.

The dental aligners 130 are trimmed to fit comfortably within the user's mouth. The dental aligners 130 are trimmed to include representations of the user's teeth and a portion of the user's gums. As described in greater detail below, the model analyzer 118 is configured to determine a cut line for the dental aligners 130 and the model analyzer 118 is configured to control the cutting system 106 to cut the dental aligners 130 along the cut line.

The model analyzer 118 may include a tooth identifier 120. The tooth identifier 120 may be a sub-circuit of the model analyzer 118. While shown as included within and a component of the model analyzer 118, in some embodiments, the tooth identifier 120 is separate from the model analyzer 118. The model analyzer 118 may also include a gingival line extractor 122, a cut line determiner 124, and a cutting system controller 126. The gingival line extractor 122, cut line determiner 124, and cutting system controller 126 may each be sub-circuits of the model analyzer 118 or, in some embodiments, may be separate from the model analyzer 118. In some embodiments, some of the components or sub-circuits may be combined or further separated.

Figure 2:
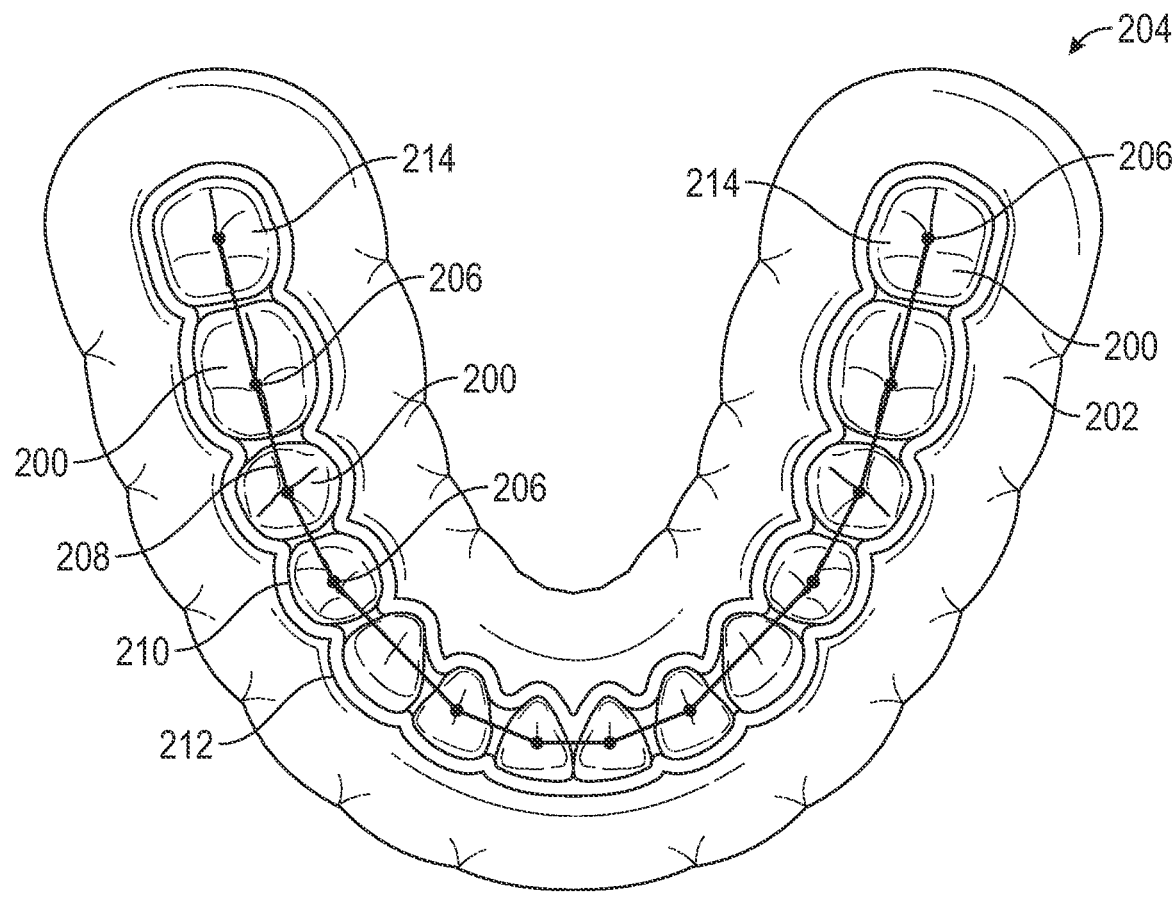
FIG. 2 is a top view of a model of a user's dentition, according to an illustrative embodiment.

Referring now to FIG. 1 and FIG. 2, the tooth identifier 120 is configured to extract the teeth 200 and gingiva 202 from the model 204 generated via the model generator 116. Specifically, FIG. 2 depicts a top view of a model 204 of a user's dentition, according to an illustrative embodiment. While described herein as teeth 200 and gingiva 202 with reference to the model 204, it is noted that the teeth 200 refer to a teeth portion 200 of the model 204 which correspond to teeth within the user's dentition, and gingiva 202 refer to a gingiva portion 202 of the model which corresponds to gingiva within the user's dentition. The tooth identifier 120 can be configured to identify the teeth within the model using a teeth identification algorithm. The teeth identification algorithm may identify various characteristics within the model which are consistent with teeth 200, such as surface contours of crowns, separation or gaps in the inter-proximal region (e.g., the space between teeth 200), etc. The tooth identifier 120 can be configured to identify the teeth 200 within the model 204 and identify the remaining portions of the model 204 which are not teeth 200 as gingiva 202.

The tooth identifier 120 may be configured to label the teeth 200 according to an identification system, such as a numbering system. The numbering system can be the universal numbering system, the Palmer numbering system, the FDI numbering system, etc. The numbering system may be used for ordering teeth 200 and locating end teeth, as described in greater detail below. The tooth identifier 120 may be configured to assign numbers to various teeth 200 based on their location within the user's dentition. Each identifier or number may be particular to a specific location of a tooth within a standard (e.g., fully developed) dentition. The tooth identifier 120 may be configured to generate an object (OBJ) file including each of the teeth 200 and gingiva 202, with each of the teeth 200 and gingiva 202 being represented as separate objects within the OBJ file.

In the model 204, each of the teeth 200 and the gingiva 202 may be positioned in an orientation along the user's dentition. The tooth identifier 120 may be configured to generate a global axis for the user's dentition. The global axis may be an axis defined along the center of mass of the user's dentition (extending in the labial/lingual direction, in the cranial/caudal direction, etc.), along the front-most or rear-most points of the user's dentition, etc. The tooth identifier 120 may be configured to define or identify orientation data corresponding to an orientation of each of the objects with respect to the global axis. Each object may be separately defined within the OBJ file and include the orientation data.

In some embodiments, the tooth identifier 120 is configured to identify a reference point 206 for each of the teeth 200 in the model 204. The reference points 206 may be used for defining the cut line, as described in greater detail below. In some embodiments, the reference points 206 may be the centroids, or center of mass, for each of the teeth 200. As used herein, reference point and centroid are used interchangeably, though it will be appreciated that a reference point does not need to be a centroid of a tooth or related to a center of mass of a tooth. The tooth identifier 120 may be configured to determine a two-dimensional centroid (e.g., from the overhead view shown in FIG. 2) for each of the teeth 200. In some embodiments, the tooth identifier 120 may be configured to connect each of the centroids 206 to generate a dental arch line 208. The dental arch line 208 may also be used for defining the cut line.

The gingival line extractor 122 is configured to identify a gingival line 210 for the model 204. The gingival line 210 is defined as the juncture or interface between the teeth 200 and gingiva 202. The gingival line extractor 122 may be configured to identify the gingival line 210 by identifying a location where the teeth 200 and gingiva 202 meet. As described above, the tooth identifier 120 may be configured to identify a location of the teeth 200 within the model 204, and may identify the location of the gingiva 202 based on which portions of the model 204 are not identified as teeth 200. Similarly, the gingival line extractor 122 may identify the gingival line 210 based on where the portions of the model 204 identified as teeth 200 meet portions of the model 204 identified as gingiva 202.

The cut line determiner 124 is designed or implemented to define a cut line 212 for the dental aligner 130. The cut line 212 is a line or path which extends around the model 204 and defines a travel path for a cutting tool 128 of the cutting system 106. As described in greater detail below, the cutting system controller 126 may control the cutting tool 128 (e.g., various actuators which manipulate or otherwise move the cutting tool 128) to move along the cut line 212 to cut the dental aligner 130 from the model 204.

Figure 3A:
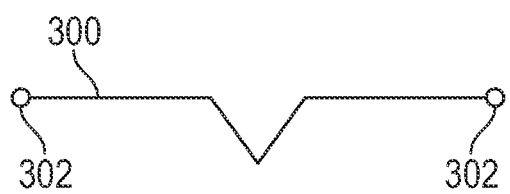
FIG. 3A and FIG. 3B depict example views of a contour with points arranged along the surface, according to illustrative embodiments.
Figure 3B:
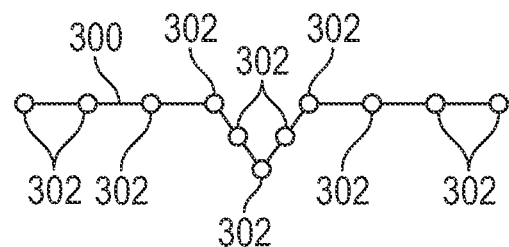

The cut line determiner 124 is configured to generate points for the cut line 212. "Points," as used herein, refers to individual points that make up the cut line 212. Each point is generated by the cut line determiner 124. FIG. 3A and FIG. 3B depict example views of a contour 300 with points 302 arranged along the surface of the contour 300. As shown in FIG. 3A and FIG. 3B, the cut line determiner 124 may be configured to generate a sufficient number of points 302 to capture contours 300 in the model 204 (e.g., on or along the surface of the model 204). In FIG. 3A, the contour 300 has insufficient points 302 to accurately capture the contour 300, as the inflection along the contour 300 does not include any points 302 and is therefore not taken into account by the cut line determiner 124 when generating a cut line. In FIG. 3B, the cut line determiner 124 has generated a sufficient number of points 302 to accurately capture the contour 300 of the model (e.g., by having at least one point 302 within the inflection of the contour 300). Embodiments using more points can provide for a more accurate cut of the aligner 130. Each point may be defined within a coordinate system with respect to, for instance, the global axis (e.g., x,y,z coordinates) to define the cut line 212, as described in greater detail below.

The cut line determiner 124 joins the points 302 together to form the cut line 212. The cut line determiner 124 may generate points 302 by identifying a location in the gingiva 202 a threshold distance from the gingival line 210. The threshold distance from the gingiva 202 is a function of the amount of space of the dental aligner 130 which is to contact, cover, or otherwise interface with the gingiva (a gingiva portion 202 of the dental aligner 130). In various implementations, the threshold distance may be relatively small such that little to no gingiva of the user's dentition is covered by or interfaces with the dental aligner 130. In such embodiments, the dental aligner 130 may not be as comfortable and may not be easily anchored within the user's mouth. In various implementations, the threshold distance may be relatively large such that a significant amount of gingiva of the user's dentition is covered by or interfaces with the dental aligner 130. In some embodiments, the threshold distance results in a dental aligner 130 that covers or interfaces with a minimal amount of the user's gingiva. Accordingly, it will be appreciated that the dental scan or impression can accurately capture the gingiva of the user, such that the trimmed dental aligner 130 conforms to the gingiva of the user.

In various implementations, the threshold distance may fall within a range of 0.5 mm and 4.0 mm. In such implementations, a relatively small amount of gingiva is covered by or interfaces with the dental aligner 130, which may balance anchoring and comfort of the dental aligner 130 with difficulty in accurately capturing gingiva in the dentition scan 108. Thus, where the threshold distance falls within the range of 0.5 mm and 4.0 mm, the cut line determiner 124 generates points in the gingiva 202 for the cut line 212 a distance from the gingival line 210 within a range (such as between 0.5 mm and 4.0 mm beneath the gingival line 210). Such a range may provide for sufficient anchoring of the dental aligner 130 by the user's gingiva while still limiting the amount of gingiva covered by or interfacing with the dental aligner (thus limiting the level of detail required for accurately representing the gingiva in the dentition scans and the aligner 130).

In some embodiments, the cut line determiner 124 generates points 302 by identifying locations that are a distance from the gingival line 210 and in regard to the reference points 206. For instance, the cut line determiner 124 may identify locations for points aligned with both the reference point 206 and the gingival line 210 (e.g., moving radially outward from the reference point 206).

In some embodiments, the cut line determiner 124 generates points by identifying locations that are a distance (e.g., 1.5 mm) from the gingival line 210 without regard to the reference points 206. For instance, the cut line determiner 124 computes or determines the cut line 212 based on the gingival line 210. As described in greater detail below, the cut line determiner 124 may offset the cut line 212 from the gingival line 210 by identifying points in the gingiva 202 a distance from the gingival line 210 along the surface of the model 204 to create the cut line 212.

Figure 4A:
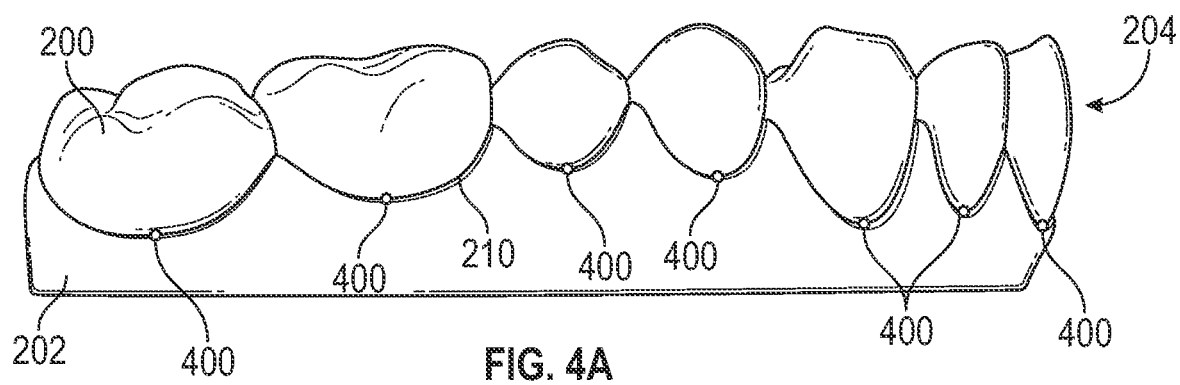
FIG. 4A and FIG. 4B depict the labial and lingual sides of a model of a user's dentition, respectively, according to an illustrative embodiment.
Figure 4B:
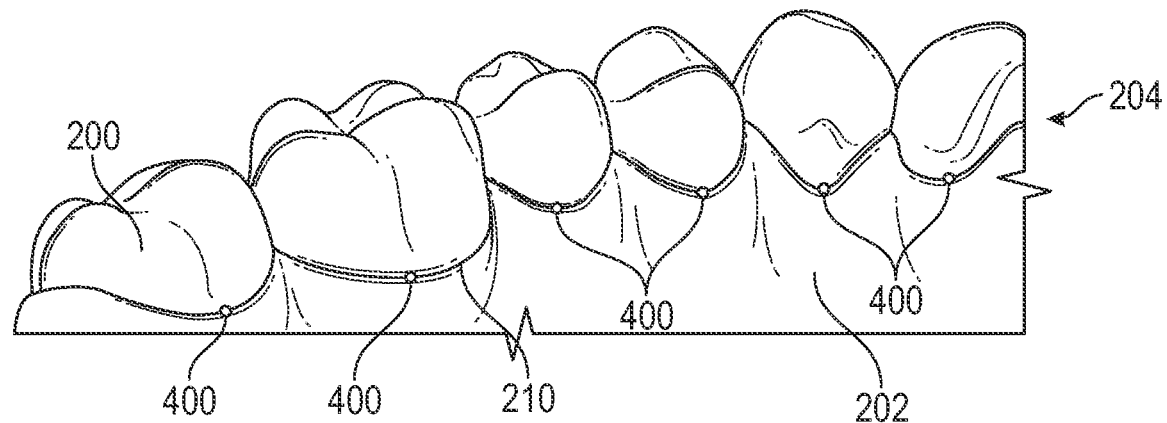

Referring now to FIG. 4A and FIG. 4B, the cut line determiner 124 is configured to generate points based on the lingual and labial lowest point of the tooth 200/gingiva 202. Specifically, FIG. 4A and FIG. 4B depict the labial and lingual side of the model 204, respectively. The cut line determiner 124 is configured to identify the lingual and labial lowest points 400 for each tooth 200 in the model 204. The cut line determiner 124 is configured to determine the labial and lingual sides of each tooth 200 within the model 204 based on the orientation data corresponding to each object within the OBJ file. The cut line determiner 124 is configured to define a line-around-tooth (LAT) for each tooth. The LAT may be defined based on the intersection of the teeth 200 and gingiva 202. Hence, the LAT for each tooth 200 may extend around the tooth 200 at the gingival line 210 for the tooth 200.

Figure 5:
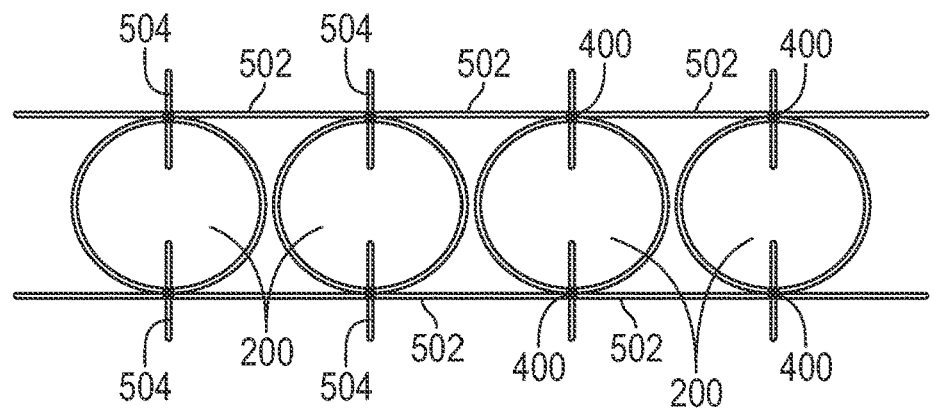
FIG. 5 is a simplified top-down diagram of a plurality of teeth within a model of a user's dentition, according to an illustrative embodiment.

Referring now to FIG. 5, a simplified top-down diagram of a plurality of teeth 200 within the model 204 is shown according to an illustrative embodiment. Each of the teeth 200 may be represented by the LAT 500. While shown as circular, it is noted that the LAT 500 may generally follow the outer profile for a respective tooth 200 and that circles are shown for representative purposes. The cut line determiner 124 may be configured to represent each of the lowest points 400 on the LAT 500. The cut line determiner 124 may be configured to define segments 502 between each of the teeth 200 along the labial-labial (and lingual-lingual) division changes from the lowest points 400 between two teeth 200. The cut line determiner 124 may be configured to join each of the segments 502 together along a respective side of the model (e.g., adjacent labial-labial segments 502 and adjacent lingual-lingual segments 502) to form a modified gingival line that extends between adjacent lowest points 400. The cut line determiner 124 may be configured to define a threshold distance from the lowest points 400 on the labial and lingual side each tooth 200. The cut line determiner 124 may define a perpendicular segment 504 at each lowest point 400 which is aligned with a centroid (for instance) of the respective tooth 200 and the lowest point 400. The perpendicular segment 504 may extend radially outwardly from the centroid and bisect the lowest point 400 on each side of the tooth 200. The perpendicular segment 504 may extend a distance from the LAT 500 (such as, for instance, 1.5 mm). The outermost point from the LAT 500 on the perpendicular segment 504 may be used for selecting points for the cut line 212. For instance, the points may be arranged between two outermost points on the perpendicular segment 504. In some embodiments, the points may be arranged parallel with the segments 502. In other embodiments, the points may be located at a distance from the segments 502 but no closer to the segment than the two adjacent outermost points on the adjacent perpendicular segments 504.

In some instances, a person may have missing teeth reflected in the model 204. The cut line determiner 124 may be configured to compensate for missing teeth within the model 204 by identifying a distance between two adjacent LATs. Where the distance exceeds a threshold (e.g., corresponding to an average distance between two adjacent teeth 200), the cut line determiner 124 may be configured to bridge the gap to connect the cut line 212.

In each of these embodiments, the cut line determiner 124 is configured to select points in the gingiva 202 a threshold distance from the gingival line 210 for forming the cut line 212. As can be best seen in FIG. 6, which shows a perspective view of the model 204 focusing on the interproximal region 600 between two teeth 200, in some implementations, the cut line 212 may not follow the interproximal region 600 between two adjacent teeth 200. Rather, the cut line 212 may be "flat" such that the cut line 212 extends in a relatively straight line along the interproximal region 600 between two teeth 200. Such embodiments may provide for a better fitting, more comfortable aligner 130.

In some embodiments, the cut line determiner 124 is configured to generate multiple cut lines 212. The cut line 212 may be a first cut line 212, and the cut line determiner 124 can also generate a second cut line 216 and a third cut line 218. Each of the first cut line 212, second cut line 216, and third cut line 218 may be at a different threshold distance from the gingival line 210. The first cut line 212 may be furthest from the gingival line 210, the third cut line 218 may be nearest to the gingival line 210, and the second cut line 216 may be between the first cut line and the third cut line 218. In such embodiments, the same model 204 may be used and reused for generating a plurality of dental aligners 130. For instance, three different types of thermoforming materials may be thermoformed to the model 204 in accordance with the sub-stages of the treatment plan. The first cut line 212 may be used for cutting the first thermoforming material thermoformed to the model 204, the second cut line 212 may be used for cutting the second thermoforming material subsequently thermoformed to the model 204, and the third cut line 212 may be used for cutting the third thermoforming material subsequently thermoformed to the model 204. By locating the cut line 212 at different threshold distances from the gingival line 210, the cutting tool 128 can cut into the model 204 along each cut line but the model 204 can still be reused for thermoforming and cutting subsequent dental aligners 130 without needing to cut or remove thermoformed material from the cut marks left in the model 204 by the cutting tool 128 (e.g., since each subsequent cut is located closer to the gingival line 210). In other embodiments, the cut line determiner 124 locates the cut line 212 at substantially the same position with respect to the gingival line 210 and the cutting tool 128 is configured to cut deeper for each subsequent cut from the same model 204 to remove material that thermoforms into the cut marks left in the model 204 during the previous cut.

Figure 6:
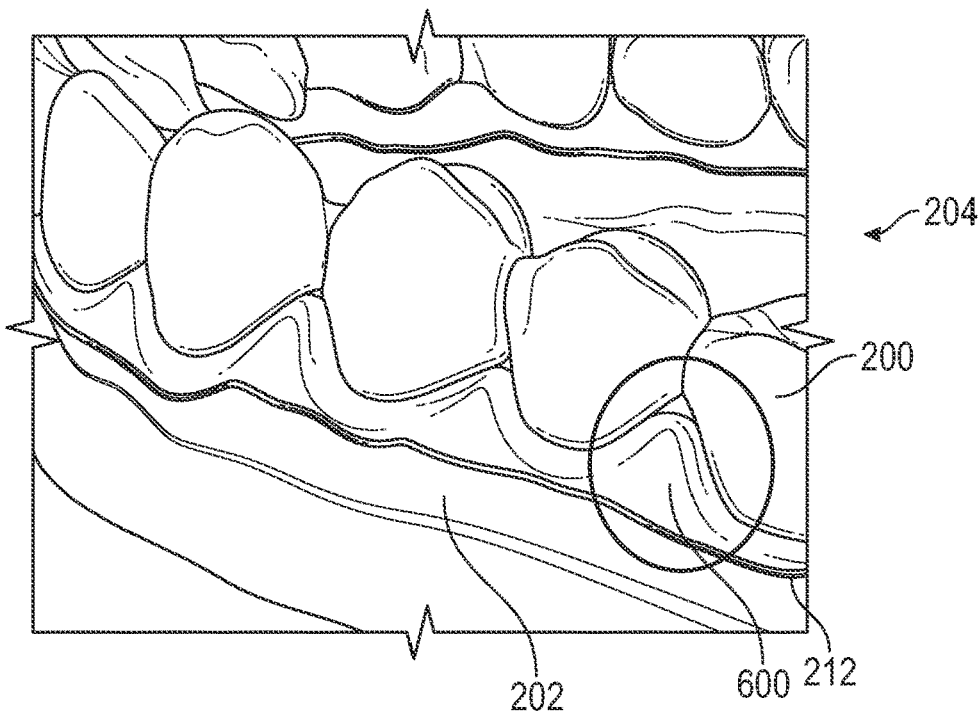
FIG. 6 is a perspective view of a model of a user's dentition focused on the interproximal region between two teeth in the model, according to an illustrative embodiment.
Figure 7:
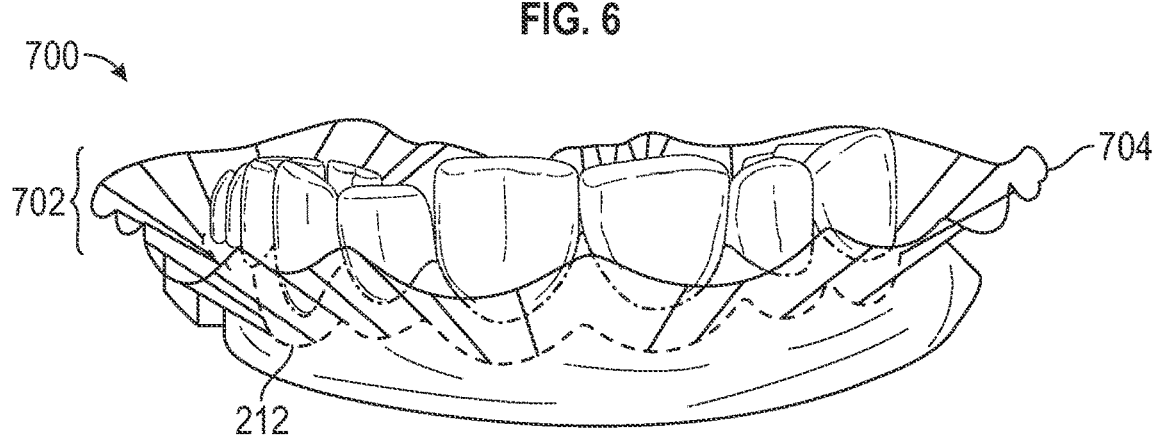
FIG. 7 is a front perspective view of a model of a user's dentition, according to an illustrative embodiment.
Figure 8:
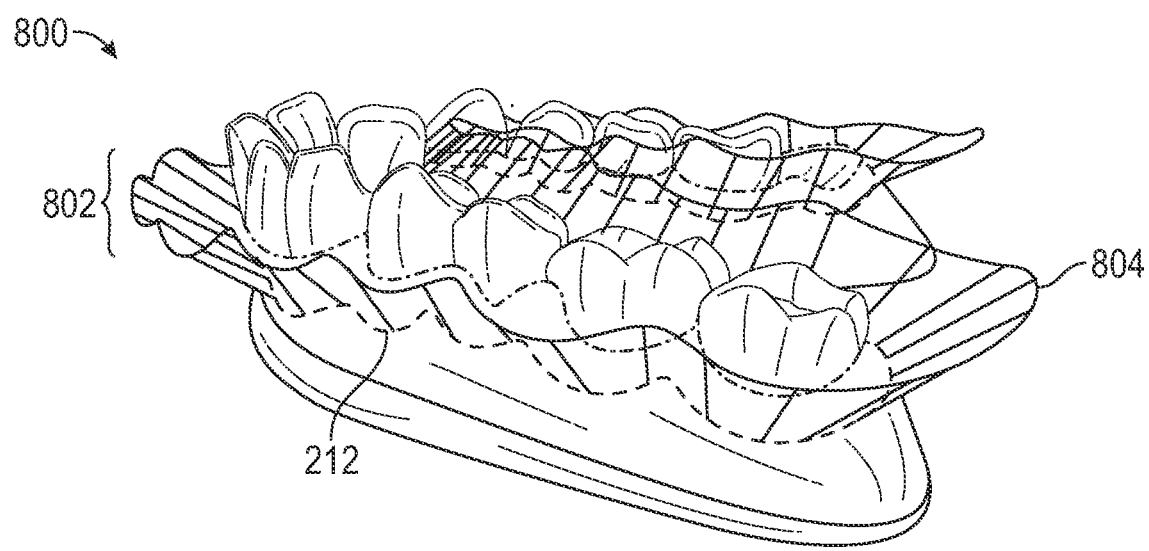
FIG. 8 is a back perspective view of one side of a model of a user's dentition, according to an illustrative embodiment.
Figure 9:
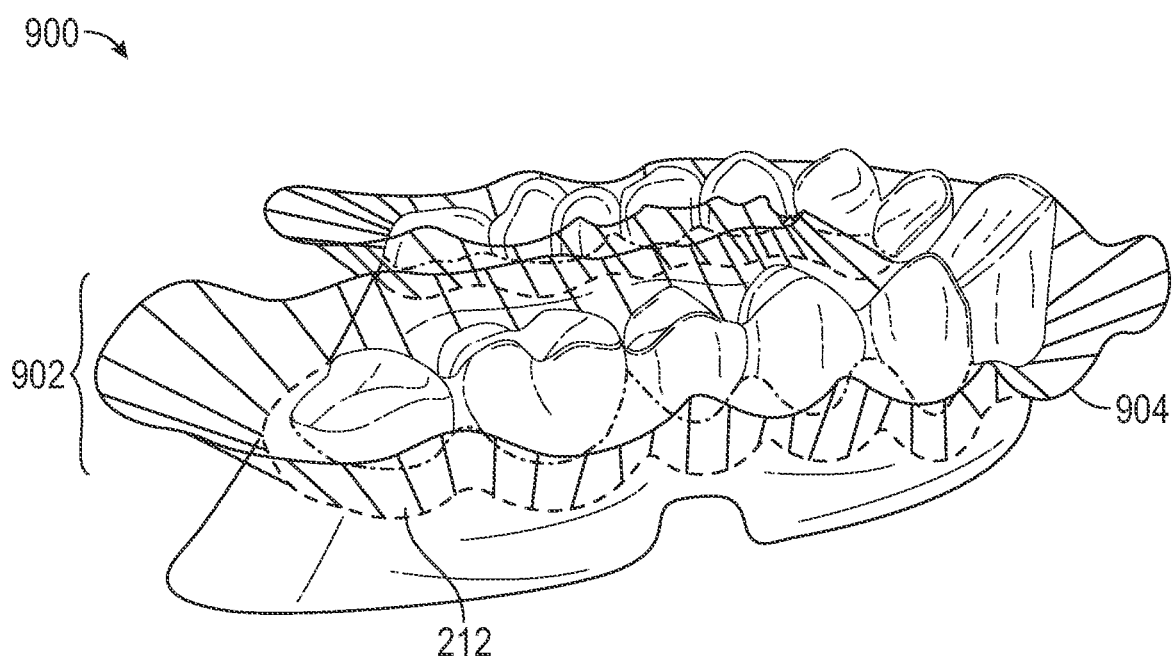
FIG. 9 is a back perspective view of another side of a model of a user's dentition, according to an illustrative embodiment.
Figure 10:
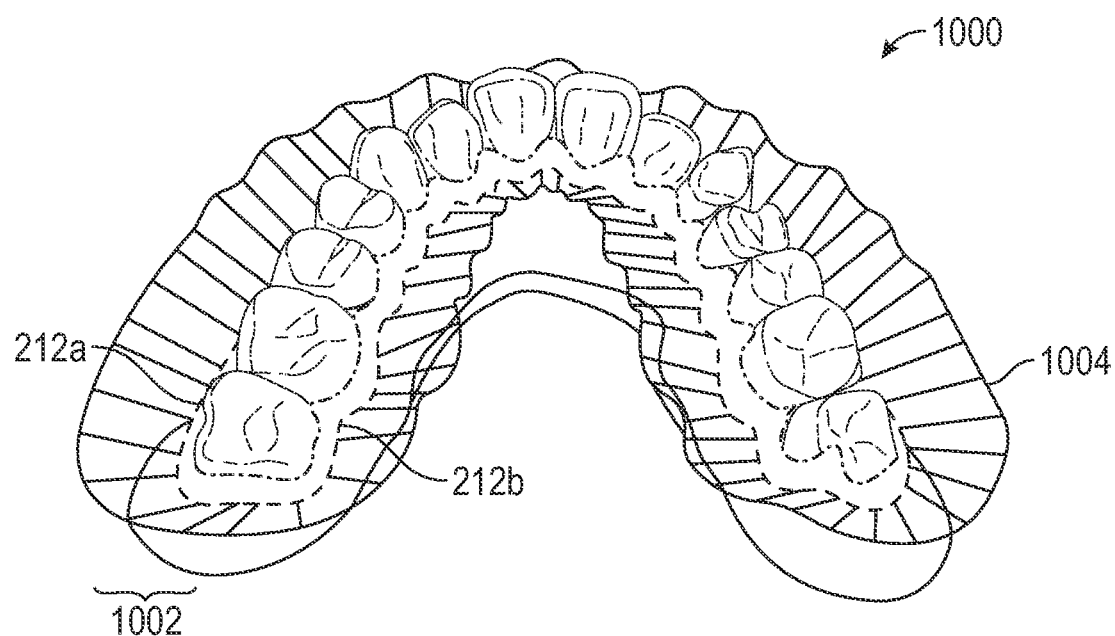
FIG. 10 is a rear perspective view of a model of a user's dentition, according to an illustrative embodiment.

The cut line determiner 124 may be configured to define the proximity of the cut line 212 with respect to the interproximal region 600 based on a determined or selected percentage of the LAT used to define the gingival margin. In some embodiments, a user (such as a dental technician) may modify one or more parameters (such as the percentage of the LAT, the intersection point between the LAT and gingival line 210, and so forth) to modify the proximity of the cut line 212 with respect to the interproximal region 600. In some embodiments, the cut line 212 is flattened as lesser amounts of the LAT is used for defining the cut line 212. For example, when the cut line 212 is defined based on using 100% of the LAT, the cut line 212 is more scalloped (e.g., the cut line 212 significantly follows the curvature of the teeth 200 and extends deepest into the interproximal region 600 between the teeth 200). In another example, when the cut line 212 is defined based on using a lesser amount of the LAT, the cut line 212 is semi-scalloped (e.g., the cut line 212 follows the curvature of the teeth 200 but only slightly extends into the interproximal region 600 between the teeth 200). In another example, when the cut line 212 is defined based on using an even lesser amount of the LAT, the cut line 212 is flatter, flat, or substantially flat compared to the scalloped or semi-scalloped cut lines 212 (e.g., the cut line 212 minimally follows the curvature of the teeth 200 and does not extent into the interproximal region 600 between the teeth 200, as shown in FIG. 6).

Referring now to FIG. 1 and FIG. 7-FIG. 11, the cut line determiner 124 is configured to join the plurality of points together to form, generate, or otherwise define the cut line 212. FIG. 7-FIG. 11 show various views of three-dimensional models 700, 800, 900, 1000 corresponding to the model 204, according to illustrative embodiments. As described above, the cut line 212 extends around the model 204 and defines a travel path 702 for the cutting tool 128 of the cutting system 106. The travel path 702 extends outwardly from the model 204 at an angle that defines an angle of the cutting tool 128 with respect to the dental aligner 130. The angle may be an angle with respect to a normal vector from points of the cut line 212. Such an angle may be less than, for instance, 90°. In some embodiments, the angle may follow the normal vector. In some embodiments, the cut line determiner 124 may determine the normal vector for each of the points of the cut line 212, and the may remove z-components of the normal vector (e.g., the z-component extending parallel to the sagittal, or longitudinal plane) for defining the angle of the cutting tool 128 with respect to the cut line 212. The tip of the cutting tool 128 may be positioned along the outer edge 704, 804, 904, 1004 of the travel path 702, 802, 902, 1002 and may extend towards the dental aligner 130 and the model 204 at the angles shown extending outwardly from the models 700, 800, 900, 1000 and connecting the cut line 212 to the outer edge 704, 804, 904, 1004.

In some embodiments, the cut line determiner 124 is configured to apply a smoothing algorithm to smooth the cut line 212. The cut line determiner 124 is configured to apply the smoothing algorithm to various portions of the cut line 212 or the entirety of the cut line 212. The cut line determiner 124 may be configured to apply the smoothing algorithm to smooth the cut line 212 adjacent to an interproximal region between two teeth 200 of the model 204. Such areas may be prone to tear. Thus, the cut line determiner 124 may be configured to smooth the cut line 212 to eliminate steep cut-ins for the dental aligner 130 at the interproximal region.

In some embodiments, the cut line determiner 124 is configured to identify a rear (or terminal) molar 214 in the model 204. The cut line determiner 124 is configured to identify the rear molar 214 based on the number assigned to the teeth (e.g., by the tooth identifier 120). The cut line determiner 124 is configured to identify the rear molar 214 based on the last tooth present in the model 204 (which may or may not be the third molar). The cut line determiner 124 is configured to connect the cut line 212 for the outer portion of the dental aligner 130 (e.g., the labial cut line 212a) and the cut line 212 for the inner portion of the dental aligner 130 (e.g., lingual cut line 212b). Hence, the cut line 212 may generally include a labial cut line 212a and lingual cut line 212b, and a connecting cut line 212c that connects the labial cut line 212a and the lingual cut line 212b (as can be best seen in FIGS. 10-11).

Figure 11:
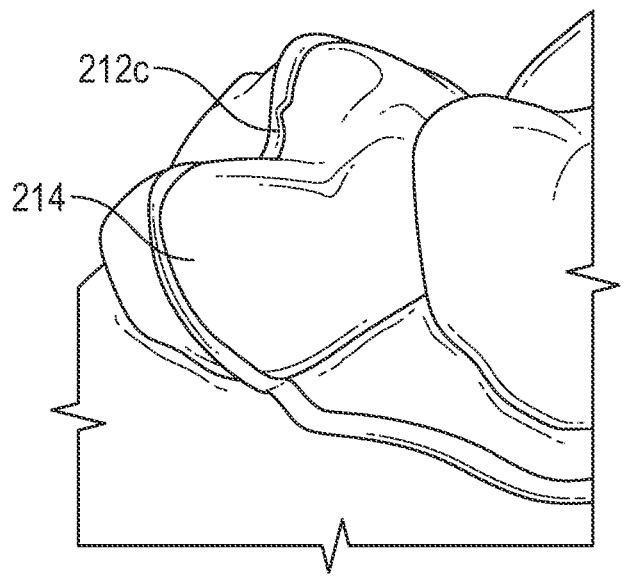
FIG. 11 is a back perspective view of rear molars of a model of a user's dentition, according to an illustrative embodiment.

In some embodiments, the cut line determiner 124 is configured to define the connecting cut line 212c by wrapping the connecting cut line 212c around the rear molar 214 (e.g. as shown in FIG. 11) within the gingiva 202. In some embodiments, the cut line determiner 124 defines the connecting cut line 212c wrapping around the rear molar 214 to form a feature around the rear molar 214 in the gingiva portion 202 of the dental aligner 130. In some embodiments, the feature is formed by resting the cutting tool 128 on a portion of the gingiva portion 202 of the aligner 130 or by moving the cutting tool 128 back and forth across the same cut line or within an area of the gingiva portion 202 of the aligner 130. In some embodiments, the feature is formed in a teeth portion 134 of the aligner. The cut line determiner 124 may be configured to increase a space between the cut line 212c and the gingiva line 210 to provide space for the cutting tool 128 to form the feature. The feature can be used as an anchoring portion (e.g., for a fixture tray or a manipulator component of the cutting tool 128). In some embodiments, the feature is a portion of the aligner 130 that includes the material of the model 204 blended with a material of the aligner 130. The portion of the aligner 130 with blended material can be later removed during the fabrication process. In some embodiments, the cut line determiner 124 defines the connecting line 212c taper the connecting line 212c around the rear molars 214 of the model 204.

In some embodiments, the cut line determiner 124 is configured to define the connecting cut lines 212c by crossing the connecting cut line 212c over the top (e.g., the crown) of the rear molar 214. The connecting cut line 212c may cross over a portion of the rear molar 214. In some embodiments, the cut line determiner 124 may cross the connecting cut line 212c over half of the rear molar 214 (e.g., along the medial-distal center of the rear molar 214 as shown in FIG. 11) such that the connecting cut line 212c bisects the rear molar 214.

In some embodiments, the cut line determiner 124 is configured to perform a collision analysis using an algorithm to determine whether the cutting tool 128 for the cutting system 106 will cut a non-cutting portion of the dental aligner 130 (e.g., the teeth portion 132 for interfacing with teeth 200). The collision analysis may include defining a ray extending through the cut line and at the angle of the travel path (e.g., at the angle defined by the outer edge 704 and the cut line 212). The collision analysis may include determining whether the ray intersects or contacts any non-cutting portions of the dental aligner 130, such as teeth 200, the gingiva above the cut line 212, etc. The collision analysis may include re-defining the cut line responsive to determining that the cutting tool 128 will cut a non-cutting portion of the dental aligner 130. The cut line determiner 124 may adjust various points on the cut line 212 (e.g., including the distance between the cut line 212 and the gingival line 210) to prevent or avoid cutting a non-cutting portion of the dental aligner 130. The cut line determiner 124 may adjust the angle of the cutting tool 128 (e.g., the angle defined by the travel path 702) to prevent or avoid cutting a non-cutting portion of the dental aligner 130.

Once the cut line 212 is defined, the cutting system controller 126 is configured to control a cutting tool 128 of the cutting system 106 to cut the dental aligner 130 along the cut line 212 to prepare the dental aligner 130 for use. The cutting tool 128 may include a laser, a router, a CNC system, or other tool or system configured to cut a dental aligner 130. The cutting system 106 may include various actuators for controlling motion of the cutting tool 128. The cutting tool 128 may be configured to operate over various degrees for freedom, such as four, five, or six or more degrees of freedom. The cutting system controller 126 is configured to communicate signals to the actuators to control motion of the cutting tool 128. The cutting system controller 126 moves the cutting tool 128 to a starting position at the outer edge 704 and angles the cutting tool 128 with respect to the cut line 212 (e.g., toward the cut line 212). The cutting system controller 126 is configured to control the cutting tool 128 to cut the dental aligner 130 along the cut line 212 following the cut line 212 at the outer edge 704. Following the dental aligner 130 being cut, the dental aligner 130 may be cleaned, packaged, and shipped (e.g., either by itself or as part of a group of aligners 130) to a user. The user may wear the aligners 130 to adjust the position of the user's teeth according to the treatment plan.

Figure 12:
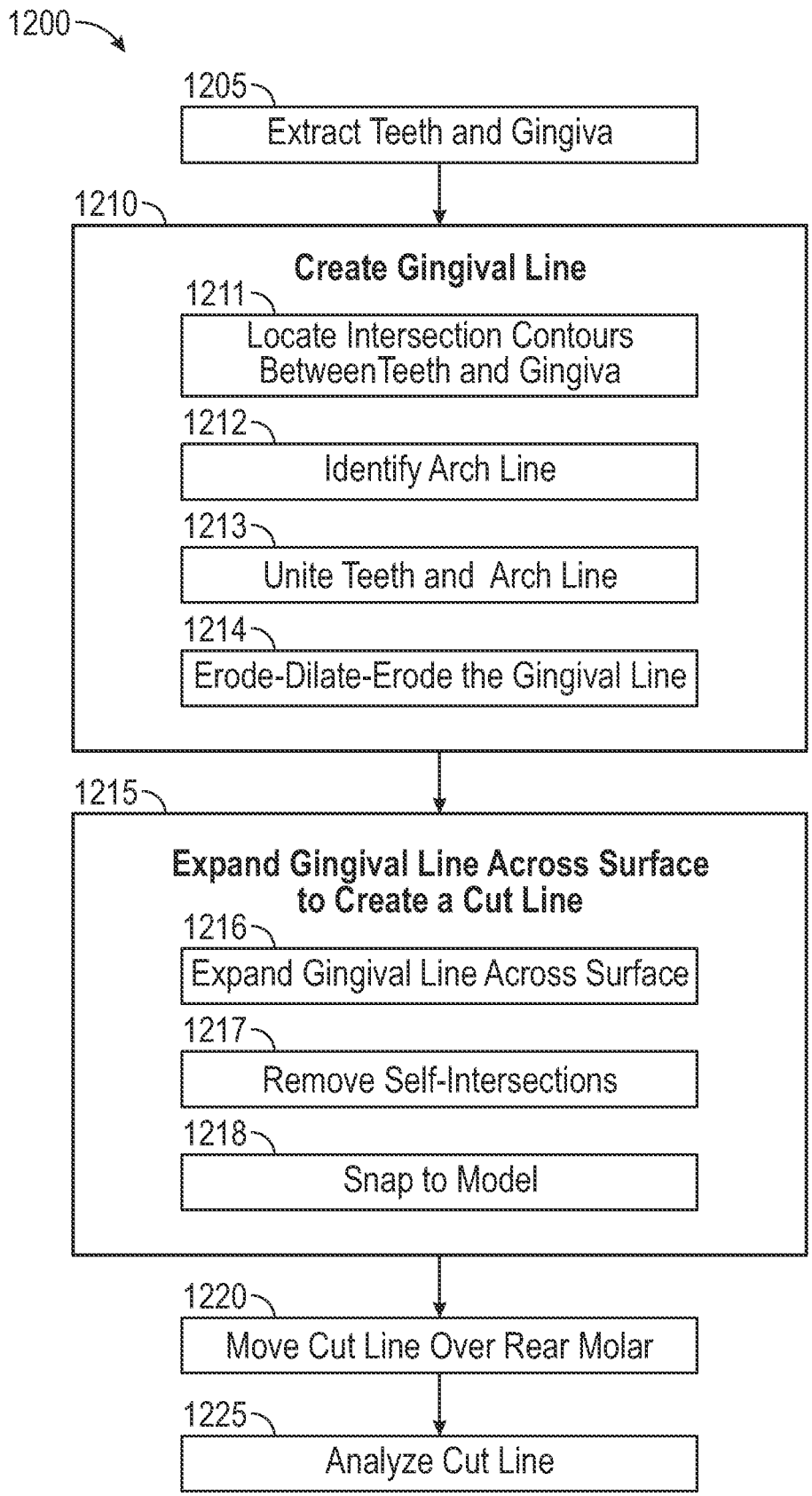
FIG. 12 is a flowchart of a method for defining a cut line, according to an illustrative embodiment.

Referring now to FIG. 12, a flowchart of a method 1200 for defining a cut line 212 is shown according to an illustrative embodiment. The method 1200 and corresponding description is one method that can be used for defining a cut line 212. The model analyzer 118 is configured to use the method 1200 or any other method to define the cut line 212.

At operation 1205, the tooth identifier 120 extracts teeth and gingiva from a model. The model may be a three-dimensional model of a user's teeth or dentition. The model may be generated by the model generator 116 based on dentition scans 108 captured via the dentition scanning system 104. The dentition scans 108 may be direct scans of a patient's dentition, or scans of a physical model or impression of the patient's dentition. The tooth identifier 120 extracts the teeth and gingiva by identifying features which are typically associated with teeth 200 (e.g., crowns on molars, separation or areas in an interproximal region, etc.) The tooth identifier 120 may identify teeth based on such characteristics and features, and assign the remaining portions of the model to the gingiva 202.

At operation 1210, the gingival line extractor 122 creates the gingival line 210 within the model. The gingival line 210 is defined as the intersection or juncture between the teeth 200 and gingiva 202 within the model.

At operation 1211, the gingival line extractor 122 locates the intersection contours between teeth 200 and gingiva 202 in the model. As can be best seen in FIG. 2 (e.g., in a top view), the intersection contours may be the contours which follow the shape of the teeth. For example, the gingival line extractor 122 may project the intersection contours onto a two-dimensional top down view. The intersection contours may follow an outer surface contour of each of the teeth (e.g., along a transverse plane of the teeth). The gingival line extractor 122 may identify the intersection contours by locating the juncture between the teeth 200 and gingiva 202. The gingival line extractor 122 may thus identify the intersection contours as the contours which define the gingival line 210.

At operation 1212, the gingival line extractor 122 identifies an arch line 208. The gingival line extractor 122 may identify the centroids 206 for each of the teeth 200. The gingival line extractor 122 may identify the centroids 206 by identifying the center of mass of each of the teeth 200. The gingival line extractor 122 may connect each of the centroids 206 to identify the arch line 208. For example, the arch line 208 may trace the centroids of the teeth 200. In some embodiments, the gingival line extractor 122 may expand a width of the arch line 208 within the top-down view (e.g., to create a polygon rather than a line). The gingival line extractor 122 may expand the width of the arch line 208 to eliminate or lessen the likelihood of the interproximal region between teeth affecting the arch line by creating multiple disjoint regions. In some embodiments, the gingival line extractor 122 may identify the arch line 208 using other methods or algorithms, such as using the intersection contours in constructing the arch line 208 and defining the arch line 208 via a high-order function.

At operation 1213, the gingival line extractor 122 unites the teeth 200 with the arch line 208. The gingival line extractor 122 may unite the two-dimensional teeth (e.g., within the top down view, such as the view shown in FIG. 2) with the arch line 208 identified at operation 1212. The gingival line extractor 122 may snap each of the teeth 200 to the arch line 208. The gingival line extractor 122 may snap the teeth 200 to the arch line 208 at their centroids 206. The gingival line extractor 122 may union the teeth 200 with the arch line 208 to create a single gingival line 210.

At operation 1214, the gingival line extractor 122 manipulates the gingival line 210 to join each of the teeth 200 together. For example, the gingival line extractor 122 may erode-dilate-erode the gingival line 210. The gingival line extractor 122 may erode the gingival line (e.g., decrease the size of the gingival line 210, or shrink the gingival line 210) to smooth the shape of the gingival line 210. The gingival line extractor 122 may dilate the gingival line 210 (e.g., expand or increase the size of the gingival line 210) an amount or percentage (e.g., 10%, 20%, 50%) to connect neighboring teeth 200 (even without the arch line 208 being united with the teeth 200). The gingival line extractor 122 may then erode the gingival line 210 to a size similar to or the same as the gingival line 210 prior to execution of operation 1214 (e.g., back to the original size). Each of the teeth may be joined together due to eroding-dilating-eroding the gingival line 210.

At operation 1215, the cut line determiner 124 expands the gingival line 210 across the surface of the model 204 to create the cut line 212. The cut line determiner 124 expands the gingival line 210 across the surface of the model 204 to create the cut line 212 for the model 204.

At operation 1216, the cut line determiner 124 expands the gingival line 210 across the surface of the model. The cut line determiner 124 identifies points a distance within the gingiva 202 from the gingival line 210. The distance may be, for instance, 1.00 mm, 2.00 mm, 2.50 mm, 4.00 mm, etc., from the original position of the gingival line 210. Thus, the gingival line 210 is expanded into the gingiva 202 from the gingival line 210 and tracks the shape of the teeth 200. The cut line determiner 124 expands the gingival line 210 across the surface in the three-dimensional model (e.g., shown in FIG. 7-FIG. 11). For each point on the gingival line 210, the cut line determiner 124 may generate a rectangle with a surface normal corresponding to a tangent of the gingival line 210 at the respective point. The cut line determiner 124 may locate intersection edges between the gingiva 202 and the generated rectangle. The cut line determiner 124 may trace from a point on the gingiva line 210 along the gingiva 202 until the expansion distance is reached (thus expanding the gingival line 210 into the gingiva 202 along the surface of the model).

At operation 1217, the cut line determiner 124 removes self-intersections of the expanded gingival line 210. Self-intersections include intersections between the gingival line 210 for one tooth as it is expanded into the gingiva 202 and the gingival line 210 for an adjacent tooth. The cut line determiner 124 may convert the gingival line 210 to a two-dimensional representation to remove the self-intersections. Viewing the top down view shown in FIG. 2, where the gingival line 210 for each of the teeth is expanded outwardly, the gingival line 210 of one tooth may intersect with a neighboring tooth or neighboring gingival line 210. The cut line determiner 124 removes overlapping portions of the gingival line 210 at intersections of the overlapping portions of the gingival line 210. Thus, the cut line determiner 124 removes the self-intersections and overlapping portions of the expanded gingival line 210 such that the expanded gingival line 210 tracks the shape of the teeth except near the interproximal region where intersections would likely occur.

At operation 1218, the cut line determiner 124 snaps, overlays, draws, covers, or otherwise incorporates the expanded gingival line 210 into the model 204 to create the cut line 212. For each point on the two-dimensional gingival line 210 (e.g., shown in FIG. 2), the cut line determiner 124 may perform a distance weighted averaging with the three-dimensional points (e.g., within the model generated via the model generator 116) to assign a z-value. In some embodiments, the cut line determiner 124 applies a smoothing algorithm to the two-dimensional gingival line 210 with the assigned z-values. The cut line determiner 124 may incorporate the two-dimensional gingival line 210 with z-values into the three-dimensional model to define the cut line 212.

At operation 1220, the cut line determiner 124 moves the cut line 212 over the rear molars 214. The cut line determiner 124 may identify the rear molars 214 based on the number assigned to the teeth (e.g., by the tooth identifier 120 described above). The cut line determiner 124 may identify the rear molar 214 based on the last tooth present in the model 204 (which may or may not be the third molar). The cut line determiner 124 connects the cut line 212 for the outer portion of the dental aligner 130 (e.g., the labial cut line 212a) and the cut line 212 for the inner portion of the dental aligner 130 (e.g., lingual cut line 212b). The cut line determiner 124 connects the cut lines 212a, 212b by crossing the cut line 212 over the top (e.g., the crown) of the rear molar 214. The cut line 212 may cross over a portion of the rear molar (such as half of the rear molar 214). The cut line determiner 124 may cross the cut line 212 over the rear molars 214 such that the cut line 212 bisects the centroid 206 for the rear molars 214. Such embodiments may increase comfort of the resulting dental aligners 130 when worn by the user.

At operation 1225, the cut line determiner 124 analyzes the cut line 212. The cut line determiner 124 may analyze the cut line 212 to determine whether any cuts will cut a non-cutting portion of the dental aligners 130. The non-cutting portion includes, for instance, portions of the aligner 130 which surround or are adjacent to teeth. For example, the non-cutting portion of the dental aligners 130 may include each of the teeth portion 134 of the dental aligners 130, or portions of the dental aligners 130 which touch, surround, or interface with the teeth of the user. The cut line determiner 124 may perform a collision analysis to determine whether the cutting tool 128 will cut the non-cutting portion of the dental aligners 130. The cut line determiner 124 calculates a derivative of the cut line 212. The cut line determiner 124 smooths the derivate of the cut line 212. The cut line determiner 124 then computes a vector associated with the cutting tool 128. The vector is associated with the angle of the cutting tool 128 with respect to the dental aligner 130. The cut line determiner 124 computes the vector for each point on the derivative of the cut line 212. The cut line determiner 124 then removes all vertical components (e.g., components which are parallel to the sagittal plane) of the cut line 212 normal, thus eliminating cuts to non-cutting portions of dental aligners 130.

Figure 13:
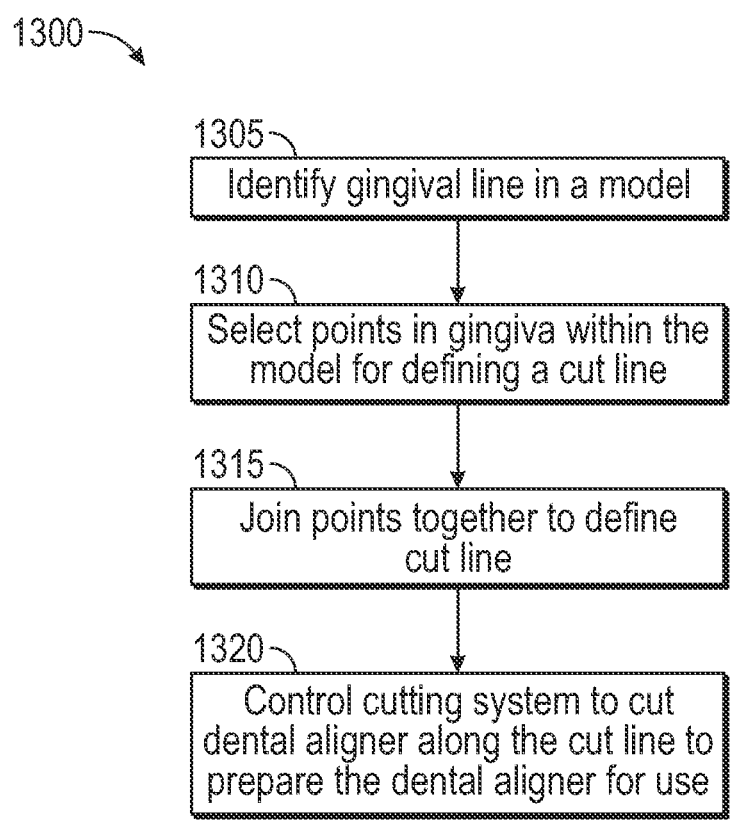
FIG. 13 is a flowchart of a method of cutting a dental aligner, according to an illustrative embodiment.

Referring now to FIG. 13, a flowchart of a method 1300 of cutting a dental aligner 130 is shown according to an illustrative embodiment. The method 1300 may be implemented by any combination of the components described herein.

At operation 1305, the gingival line extractor 122 identifies a gingival line 210 in a model. Operation 1305 may be similar to operation 1210 of the method 1200 described with reference to FIG. 12. For example, the gingival line extractor 122 identifies the intersection or junctures between the teeth 200 and gingiva 202, which may define the gingival line 210.

At operation 1310, the cut line determiner 124 generates points in the gingiva portions of the model 204 for defining the cut line 212. The cut line determiner 124 generates points by expanding each of the points of the gingival line 210 outwardly along the gingiva 202 a distance from the point's original location at the gingival line 210. The cut line determiner 124 may generate points a threshold distance (e.g., 1.00 mm, 1.50 mm, 2.00 mm, 4.00 mm, etc.) in the gingiva 202 (e.g., an absolute distance from or a surface distance from a centroid of a tooth) from the gingival line 210. The cut line determiner 124 may thus expand the identified gingival line 210 (e.g., identified at operation 1305) across a surface of the model (e.g., within the gingiva 202) a distance from the gingival line 210. The expanded gingival line 210 is constructed of the plurality of selected points.

At operation 1315, the cut line determiner 124 joins the points together to define the cut line 212. The cut line determiner 124 joins each of the points moved outwardly a distance from the gingival line 210 to create the cut line 212. Thus, the cut line 212 may track or trace the shape of the gingival line 210. In some embodiments, the cut line determiner 124 may apply a smoothing algorithm to smooth the cut line 212 adjacent to the interproximal region between two teeth of the model 204. Such areas may be prone to tear when used (e.g., worn) by the user. Thus, the cut line determiner 124 may smooth the cut line 212 to eliminate steep cut-ins on the dental aligner 130 at interproximal regions to eliminate or decrease the likelihood of the dental aligners 130 tearing near or at interproximal areas.

In some embodiments, the cut line determiner 124 may identify rear molars 214 within the model. The cut line determiner 124 may connect an outer portion and an inner portion of the cut line 212 by crossing the cut lines over a portion of the rear molars. Such embodiments may be similar to operation 1220 described with reference to FIG. 12.

In some embodiments, the cut line determiner 124 performs a collision analysis algorithm to determine whether the cutting tool 128 of the cutting system 106 will cut a non-cutting portion (e.g., teeth within the model) of the dental aligner 130. In some embodiments, the cut line determiner 124 calculates vectors associated with the cutting tool 128 with respect to the dental model 204 and uncut dental aligner 130 (e.g., which may be substantially the same as the normal vector of each point for the cut line 212 extending from the gingiva 202). The cut line determiner 124 may determine whether there are any vertical components of the vector (e.g., components of the vector extending parallel to the sagittal plane), which may cause the cutting tool 128 to cut the non-cutting portion of the dental aligner 130. The cut line determiner 124 may re-define the cut line 212 to remove any vertical components of the vector. Such embodiments may eliminate or decrease the likelihood of the cutting tool 128 cutting a non-cutting portion of the dental aligner 130.

The cut line 212 may be a line which extends around the model 204 and dental aligner 130 and defines a travel path for the cutting system 106, and more specifically a travel path for the cutting tool 128. The travel path may extend outwardly from the model 204 and uncut dental aligner 130 at an angle which defines the angle of the cutting tool 128 with respect to the model 204 and uncut dental aligner 130 (e.g., the vector described above).

At operation 1320, the cutting system controller 126 may control the cutting system 106 to cut the dental aligner 130 along the cut line 212. The cutting system controller 126 controls the cutting system 106 to direct the cutting tool along the travel path 702 to cut the dental aligner 130 while on the model 204 along the cut line 212. The cutting system controller 126 may communicate a starting position (e.g., a first point along the cut line 212) and a vector for the cutting tool 128, and the travel path 702. The cutting system 106 may move the cutting tool 128 to the starting position and with the vector, initiate the cutting tool 128, and move the cutting tool 128 along the travel path 702. Alternatively, the cutting system controller 126 may control actuators within the cutting system 106 directly to manipulate movement of the cutting tool 128.

Figure 15:
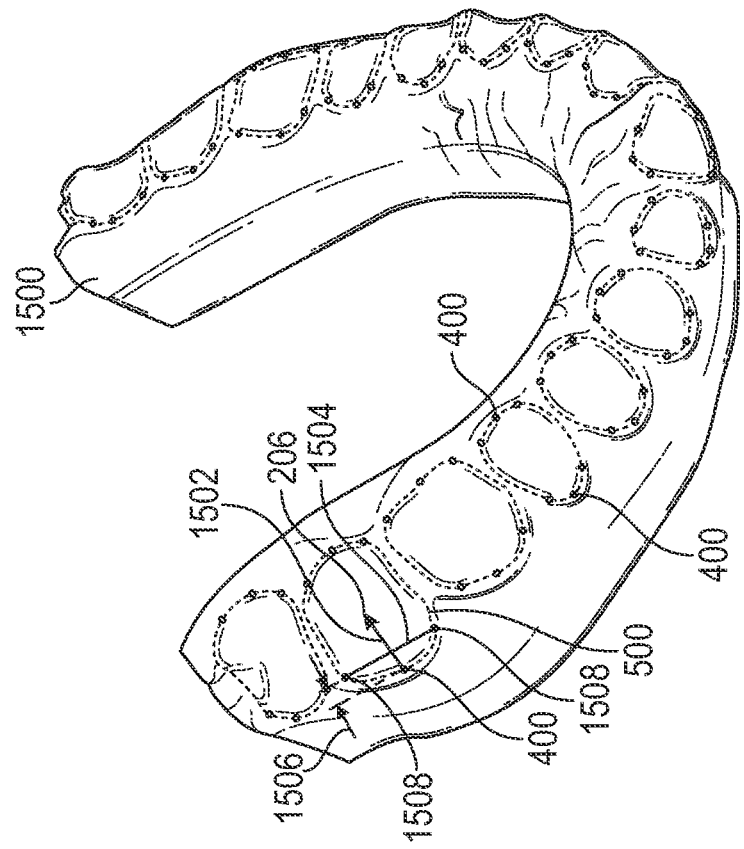
FIG. 15 is an illustration of a model of a user's dentition, according to an illustrative embodiment.

Referring now to FIG. 15, an illustration of a model 1500 of a user's dentition is shown according to an illustrative embodiment. In some embodiments, the cut line determiner 124 may be configured to determine the cut line 212 based on the reference point 206. As described above, the tooth identifier 120 may be configured to determine a reference point 206 for each tooth 200 of the model 1500. In some embodiments, the reference point 206 may be a center or centroid of the tooth 200, as shown in FIG. 2. In some embodiments, the reference point 206 may be a center of a LAT 500, as shown in FIG. 5. For example, the tooth identifier 120 may be configured to compute, calculate, determine, or otherwise identify the reference point 206 by computing an average or center of points that define a LAT 500.

The cut line determiner 124 may be configured to determine a lowest point 400 as described above with reference to FIG. 4. In some embodiments, the cut line determiner 124 may be configured to determine a lowest point 400 on both the labial and lingual sides of the teeth. The cut line determiner 124 may be configured to connect the reference point 206 and lowest point 400 using a connector 1502 (shown as an arrow extending from the lowest point 400 to the reference point 206). In some embodiments, the connector 1502 is disposed on a plane including the lowest point 400. The cut line determiner 124 may be configured to define a cut plane 1504 along the connector 1502 for determining, calculating, or otherwise defining the cut line 212, as described in greater detail below.

Figure 16:
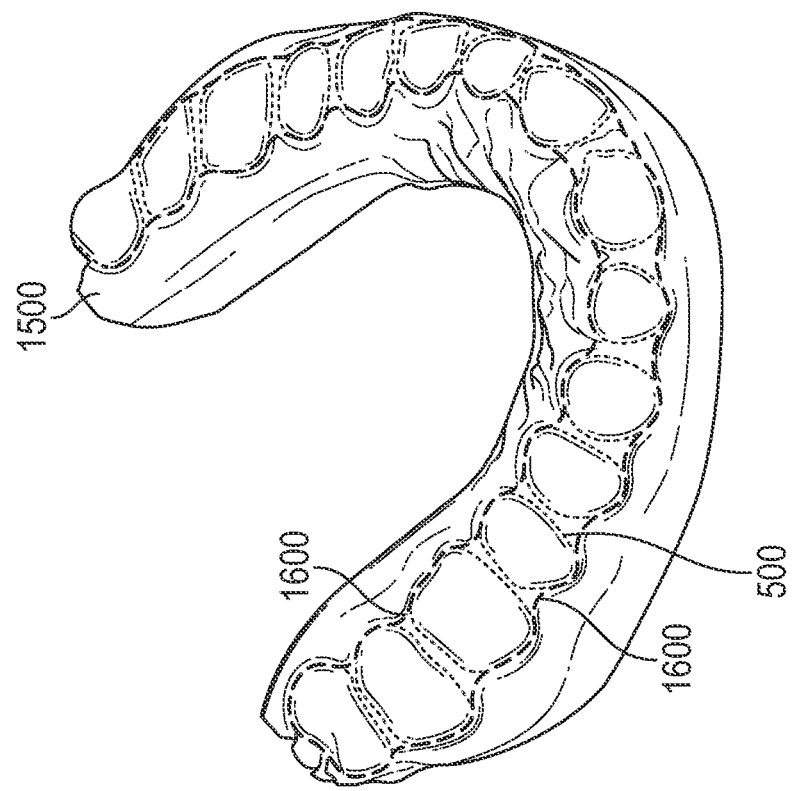
FIG. 16 is an illustration of the model of FIG. 15 including a cut line, according to an illustrative embodiment.
Figure 17:
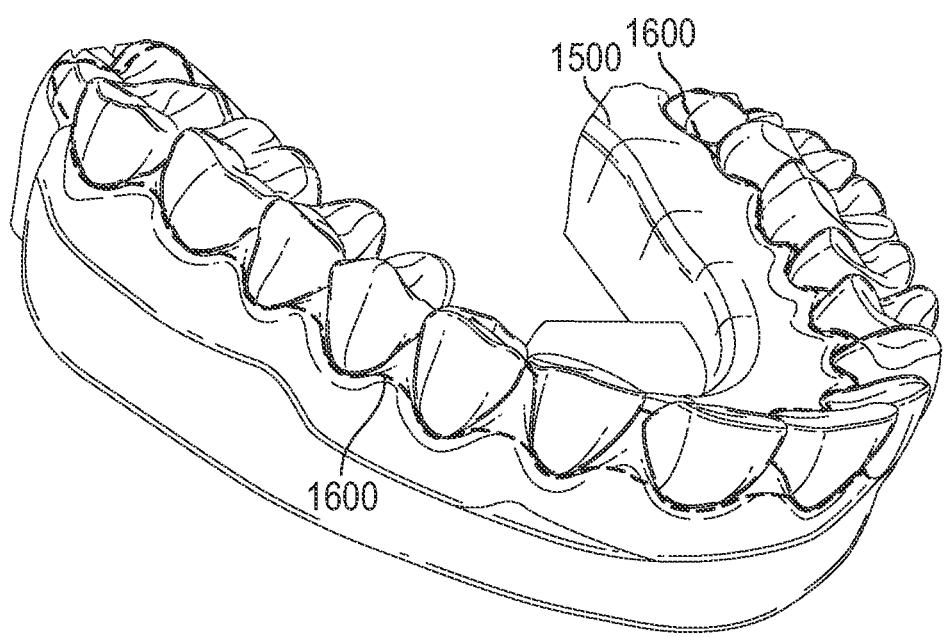
FIG. 17 is another illustration of the model of FIG. 15 including the cut line, according to an illustrative embodiment.
Figure 18:
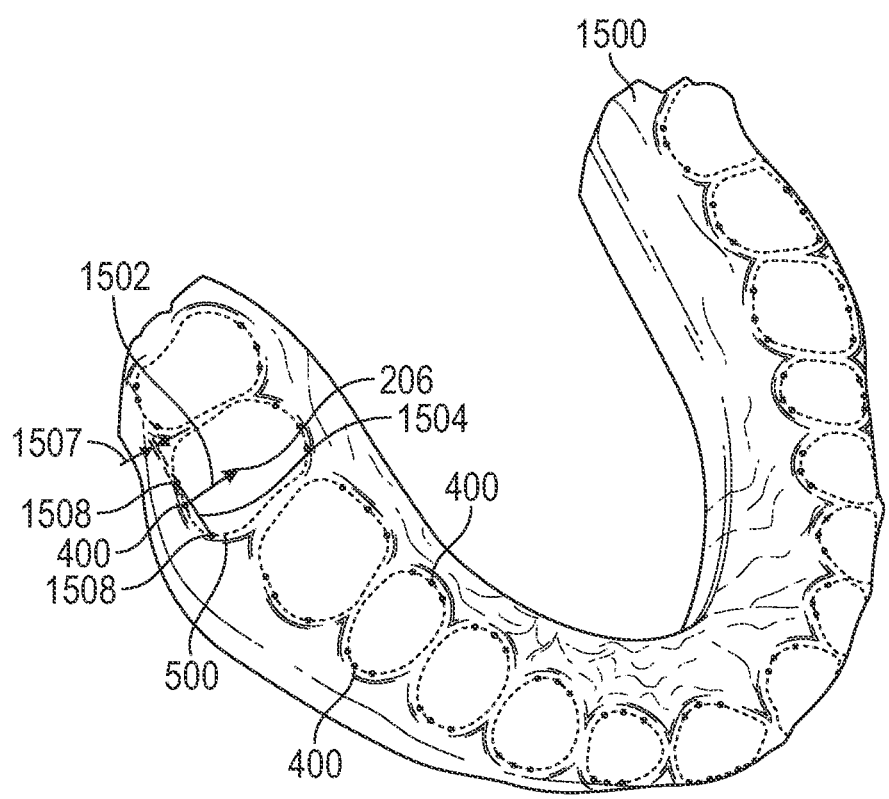
FIG. 18 is an illustration of a model of a user's dentition, according to another illustrative embodiment.
Figure 19:
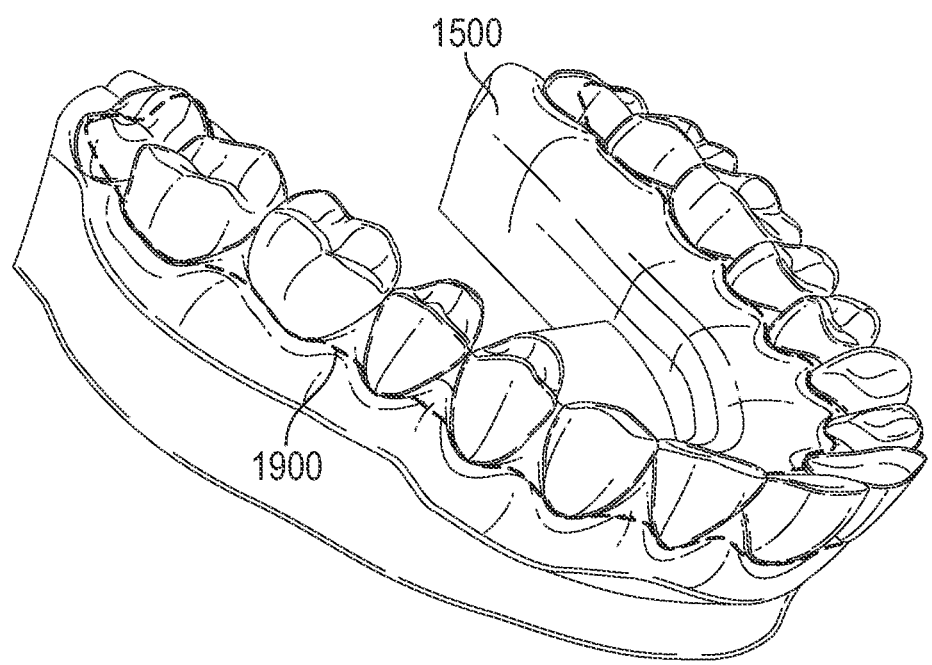
FIG. 19 is an illustration of the model of FIG. 18 including a cut line, according to an illustrative embodiment.

Referring now to FIG. 15-FIG. 19, the cut line determiner 124 may be configured to determine or identify a distance 1506 from the lowest point 400. Specifically, FIG. 16-FIG. 17 show illustrations of the model 1500 having a cut line 1600 defined based on a first distance 1506, FIG. 18 shows the model 1500 with a second distance 1507 (which is less than the first distance 1506), and FIG. 19 shows a model 1500 having a cut line 1900 based on the second distance 1507. The distance 1506, 1507 may be or include a distance from the lowest point 400 along the connector 1502. In some embodiments, the distance 1506 may be a default distance (for example, 0.5 mm, 1 mm, 2 mm, etc.). In some embodiments, the distance 1506 may be a variable distance. The distance 1506, 1507 may be set based on an analysis of the dental arch from the model 1500. For example, the distance may decrease as a complexity of treatment increases (e.g., where the teeth 200 are more crowded for example). In some implementations, the cut line determiner 124 may be configured to receive a classification of the model 1500 (e.g., from the treatment planner 114, for instance). The cut line determiner 124 may be configured to determine the distance 1506, 1507 based on the classification of the model 1500. In some embodiments, the distance 1506, 1507 may change on a tooth-by-tooth basis. In some embodiments, the distance 1506, 1507 may be a constant across each of the teeth. In some embodiments, the distance 1506, 1507 may be a constant on both labial and lingual sides of the tooth 200 (e.g., the distance 1506, 1507 from the labial-side lowest point 400 may be the same as the distance 1506, 1507 from the lingual-side lowest point 400). As described in greater detail below, the distance 1506, 1507 may define a number or portion of points from the LAT 500 which are included in the cut line 212. As shown in FIG. 16 and FIG. 17 in comparison to FIG. 19, as the distance 1506 from the lowest point 400 decreases, the cut line 212 correspondingly flattens (e.g., to become less curvy, sloped, wavy, rounded, or curvilinear), such that the cut line 1600 shown in FIG. 16 and FIG. 17 is more curved than the cut line 1900 shown in FIG. 19. Accordingly, the distance 1506, 1507 may cause the cut line 1600 to have a scalloped shape.

The cut line determiner 124 may be configured to define a cut plane 1504 using the determined or identified distance 1506, 1507. The cut line determiner 124 may be configured to define a cut plane 1504 for each tooth within the model 1500. The cut line determiner 124 may be configured to define a cut plane 1504 for the labial and lingual side of each tooth of the model 1500. The cut plane 1504 may be or include a plane that extends at an angle relative to the connector 1502. The cut plane 1504 may be defined along the connector 1502 at the distance 1506, 1507 from the lowest point 400. For example, where the distance 1506 is 1.0 mm, the cut line determiner 124 may define the cut plane 1504 along the connector 1502 at 1.00 mm from the lowest point 400. In some embodiments, the cut plane 1504 may extend perpendicular or orthogonal to the connector 1502. The cut line determiner 124 may define the cut plane 1504 along the connector 1502 beginning at the distance 1506, 1507 from the lowest point 400 and extending radially outwardly (e.g., perpendicular or orthogonal) from the connector 1502 towards the LAT 500.

The cut line determiner 124 may be configured to identify LAT points 1508 on the LAT 500 that are bisected, contacted, or otherwise located on the cut plane 1504. As shown in FIG. 15, the LAT points 1508 are located on opposing sides of the cut plane 1504 at the intersection between the cut plane 1504 and the LAT 500. The cut line determiner 124 may be configured to use the LAT points 1508 for defining the cut line 212.

The cut line determiner 124 may be configured to identify, select, or otherwise determine points on the LAT 500 for defining the cut line 212. The cut line determiner 124 may determine points on the LAT 500 that are between each of the LAT points 1508. The cut line determiner 124 may determine points on the LAT 500 which are "below" the cut plane 1504 (e.g., on a gingival-side of the cut plane 1504). For example, on the labial side of a tooth 200, the cut line determiner 124 may be configured to determine points on the LAT 500 that are between the LAT points 1508 on the gingival-side of the cut plane 1504 and include the labial-side lowest point 400. As the distance 1506 increases, more points are determined by the cut line determiner 124 for determining or defining the cut line 212. The cut line determiner 124 may determine or identify points on the LAT 500 for each tooth 200, and for both labial and lingual sides of each tooth 200, based on the cut plane 1504 defined for each tooth 200 (e.g., both on the labial and lingual side).

The cut line determiner 124 may define the cut line 212 based on the selected or determined points for each tooth 200. The cut line determiner 124 may define the cut line 212 to include each of the determined points that are located on the gingival-side of the cut plane 1504. The cut line determiner 124 may define the cut line 212 to connect labial and lingual points for two adjacent teeth 200 (e.g., labial-side points determined for a first tooth 200 connecting labial-side points determined for a second tooth 200 adjacent to the first tooth 200, and lingual-side points determined for a first tooth 200 connecting lingual-side points determined for a second tooth 200 adjacent to the first tooth 200). The cut line determiner 124 may define the cut line 212 within an interproximal region between two adjacent teeth 200, which connects determined/identified points for the two adjacent teeth 200. In some embodiments, the cut line determiner 124 may define the cut line 212 within the interproximal region by identifying a straight line that connects the LAT points 1508 that face each other on two adjacent teeth 200. The cut line determiner 124 may define the cut line 212 within the interproximal region by applying the straight line on the surface of the gingiva of the model 1500 (e.g., thereby producing a semi-curved line as a result of a straight line being applied on a sloped or non-flat surface). The cut line determiner 124 may define the cut line 212 to connect labial and lingual cut lines in a manner as described above with reference FIG. 10-FIG. 11).

Figure 20:
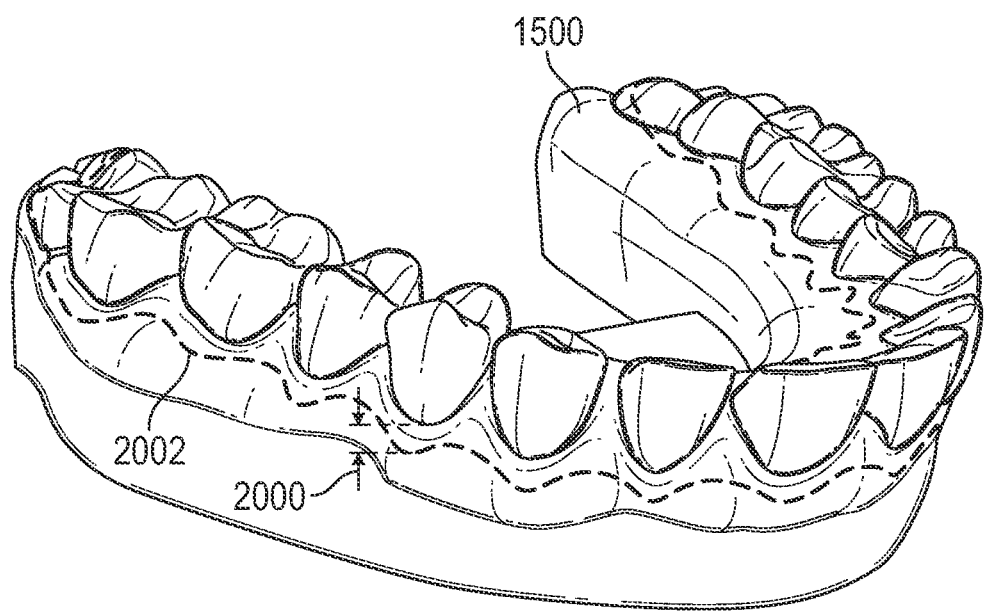
FIG. 20 is an illustration of a model of a user's dentition including a cut line at a first offset distance, according to an illustrative embodiment.
Figure 21:
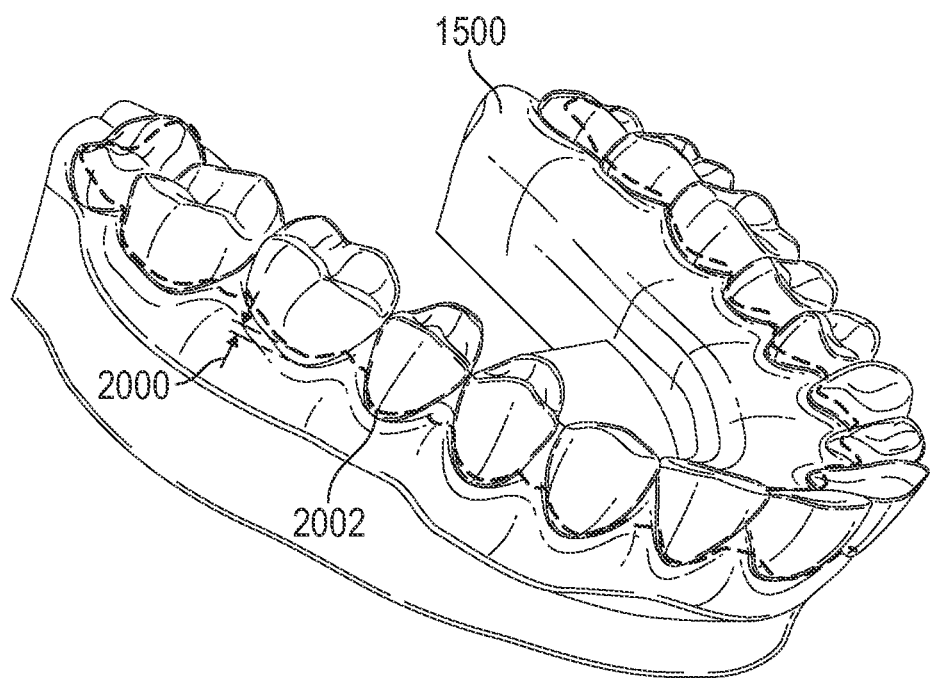
FIG. 21 is an illustration of a model of a user's dentition including a cut line at a second offset distance, according to an illustrative embodiment.

Referring now to FIG. 20-FIG. 21, in some embodiments, the cut line determiner 124 may be configured to receive an offset value for defining an offset distance 2000 of the cut line 2002 from a gingiva-tooth interface of the model 1500. Specifically, FIG. 20 shows an illustration of the model 1500 having a cut line 2002 at a first offset distance 2000, and FIG. 21 shows an illustration of the model 1500 having a cut line 2002 at a second offset distance 2000. The offset may move the cut line 2002 either toward a crown of a tooth or into the gingiva of the tooth. In some embodiments, the cut line determiner 124 may be configured to receive the offset value from a computing device (such as a computing device associated with the treatment planner 114, associated with the dentition scanning system 104, etc.). In some embodiments, the offset value may be a fixed value for each of the teeth in the model 1500 (e.g., for each teeth, both on the labial-side and the lingual side). In some embodiments, the cut line determiner 124 may be configured to receive or otherwise determine a variable offset value. For example, and similar to the embodiments described above with reference to the distance 1506, 1507, the cut line determiner 124 may be configured to receive or determine a variable offset value based on a complexity of treatment (e.g., crowding, malocclusion, etc.), based on a classification of the model 1500, etc. In some embodiments, the cut line determiner 124 may be configured to receive or determine the variable offset value on a tooth-by-tooth basis (e.g., to change the offset value as teeth are more crowded, for example). In some embodiments, the cut line determiner 124 may be configured to receive or determine the variable offset value on a labial or lingual-side basis. For example, the labial-side cut line may have a first offset value and the lingual side cut line may have a second offset value. As such, various implementations and embodiments of offset values and distances 1506, 1507 may be determined (in some instances, on a tooth-by-tooth basis) for each individual model 1500, to both provide increased comfort, less resistance to tearing, and/or to impart forces on teeth for treatment. In some embodiments, a first algorithm is used to generate a first preliminary cut line and a second algorithm different from the first algorithm is used to generate a second preliminary cut line, and then the cut line determiner 124 uses part of the first preliminary cut line and part of the second preliminary cut line to create the cut line 2002. For example, the cut line determiner 214 can generate a first preliminary cut line having a positive offset distance and generate a second preliminary cut line having a negative offset distance, and then generate the cut line 2002 using the first preliminary cut line for one or more teeth and using the second preliminary cut line for one or more teeth. In some embodiments, the cut line determiner 214 uses the first preliminary cut line for each tooth as a default and uses the second preliminary cut line for individual teeth that are selected by a user input (e.g., based on a user input from a dentist, orthodontist, or technician).

The cut line determiner 124 may be configured to define the cut line 212 based on the offset value. The cut line determiner 124 may be configured to compute cut line points based on the defined/determined points and the received offset value. For example, the cut line determiner 124 may be configured to compute the cut line points by moving each of the defined/determined points an offset distance 2000 along a surface of the model 1500 based on the offset value. As shown in FIG. 20 and FIG. 21, the offset value may be a positive or negative value, respectively. Where the offset value is a positive value, the cut line determiner 124 may compute the cut line points at an offset distance 2000 within the gingiva portion of the model 1500. Similarly, where the offset value is a negative value, the cut line determiner 124 may compute the cut line points at an offset distance 2000 within the teeth portion of the model 1500. In some embodiments, the cut line determiner 124 may compute the cut line points by shifting, for each point defined or identified as described above on the LAT 500 and in the interproximal region, the point on or along the surface of the model 1500 in the y-z direction (e.g., where the y direction is along the longitudinal axis of the body, and the z direction is along the sagittal axis of the body).

Figure 22:
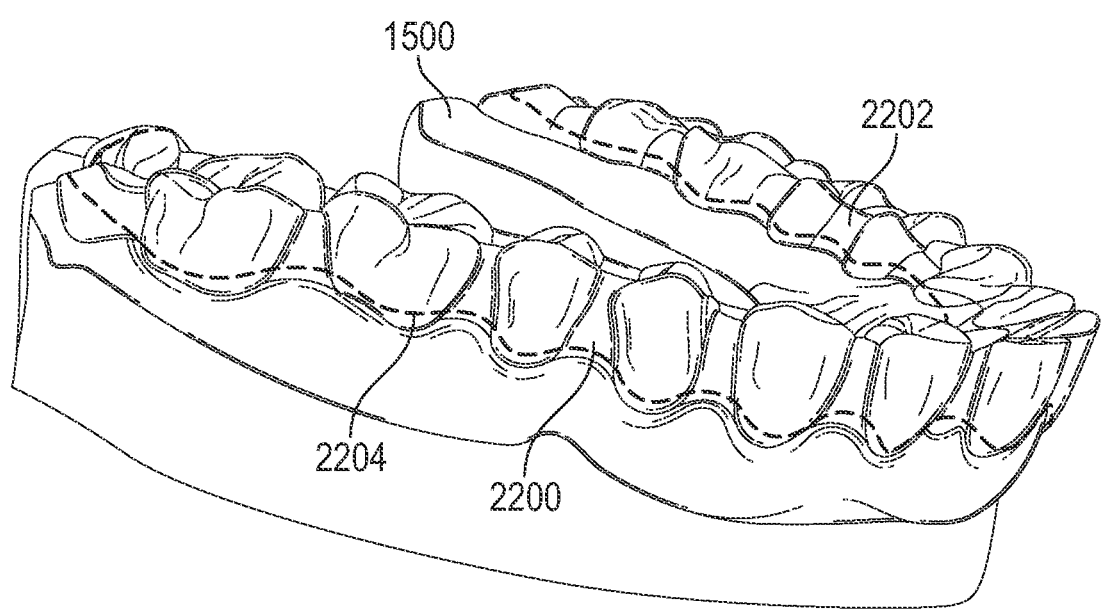
FIG. 22 is an illustration of a model of a user's dentition including interproximal virtual filler, according to an illustrative embodiment.

Referring now to FIG. 2 and FIG. 22, and in some instances where a particular model 1500 includes a void or space between teeth 200 within the interproximal region, the model generator 116 may be configured to add, incorporate, or otherwise provide interproximal virtual filler within the void or space between two adjacent teeth 200. Specifically, FIG. 22 shows an illustration of a model 1500 of a user's dentition including interproximal virtual filler 2200, 2202. The model generator 116 may be configured to provide labial and lingual-side interproximal virtual filler 2200, 2202, respectively. The cut line determiner 124 may be configured to define the cut line 2204 using the interproximal virtual filler 2200, 2202, as described in greater detail below.

In some embodiments, the model generator 116 may be configured to identify or determine a centroid 206 for each tooth 200 within the model 204. In some embodiments, the model generator 116 may be configured to determine the centroid 206 by averaging the locations of each of the vertices of the tooth 200 (e.g., similar to calculating or computing a center of mass for an object of uniform density). The model generator 116 may be configured to determine, compute, or otherwise define a three dimensional vector (shown as a connector 208, and referred to herein as "NX") beginning at a centroid 206 (referred to herein as "C0") of a first tooth 200 connecting each of the other centroids 206 (referred to herein as "C1"-"CN") of a dental arch. The model generator 116 may select, determine, or otherwise identify adjacent teeth 200 from a given tooth 200 by identifying a centroid C1 of a neighbor tooth 200 (referred to as neighbor 0 (N0)) having a shortest straight line distance along the connector 208 from the C0 of the given tooth 200 (referred to as adjacent 0 (A0)). The model generator 116 may be configured to compute, calculate, or otherwise determine a unit vector U0 from C0 to A0, and an adjacent direction vector (D0). For the next neighbor tooth 200 (e.g., Ni), the model generator 116 may be configured to compute, calculate, or otherwise determine the unit vector (Ui) between the centroid C0 and the centroid Ci of the next neighbor tooth Ni. The model generator 116 may be configured to compute, determine, or otherwise calculate a dot product (e.g., by performing a dot product operation) between U0 and Ui. Where the dot product is greater than −0.25, than the model generator 116 may be configured to define Ni as the next adjacent tooth 200 (e.g., adjacent tooth A1), and define the unit vector Ui to be the next adjacent direction vector (D1). If the dot product is not greater than −0.25, the model generator 116 may be configured to repeat computing the unit vector with the next adjacent tooth (Ni+1). Following determining A1 and D1, model generator may be configured to add, incorporate, or otherwise provide C0, A0, D0, A1 and D1 to a data structure (such as memory 112) labeled with the centroid C0's unique location coordinates (referred to herein as adjacency information "AdjSet" for adjacency set). The model generator 116 may be configured to repeat the above-mentioned steps until each of the centroids 206 have been proceed, thereby generating an AdjSet for each of the centroids 206 of the model 204.

The model generator 116 may be configured to define the labial and lingual-side virtual filler 2200, 2202 by defining two two-dimensional (2D) planes for each centroid pair 206 (e.g., of two adjacent teeth 200). The model generator 116 may be configured to define the two 2D planes that are each centered at each of centroids in the pair. The model generator 116 may be configured to orient the 2D planes such that a normal vector of each of the 2D planes align with the unit vector U which points towards the other centroid 206 in the pair. The model generator 116 may be configured to perform an intersection Boolean operation between the 2D planes and the tooth 200 models whose centroids 206 that they are centered at, which result in two two-dimensional profiles of the neighboring teeth 200 within the labial and lingual sides of the interproximal region. The model generator 116 may be configured to scale the 2D profiles to between 60%-80% their initial size. The model generator 116 may be configured to perform an edge loop bridging function to join the two 2D profiles together forming a three-dimensional object having a labial and lingual side virtual filler 2200, 2202, which acts to fill the gaps between the teeth. The model generator 116 may be configured to repeat this for each centroid pair 206 until each of the teeth 200 have been processed, such that virtual filler is added between each of the teeth 200 where gaps would otherwise be present.

The cut line determiner 124 may be configured to define the cut line 212 along the interproximal virtual filler 2200, 2202 between two adjacent teeth 200. The cut line determiner 124 may be configured to define the cut line 212 within the interproximal region, by drawing a straight line between the LAT points 1508 for two adjacent teeth, and applying the straight line to the curved surface within the interproximal region on or along the interproximal virtual filler 2200, 2202 between two adjacent teeth. Such embodiments may provide for a dental aligner 130 that has a negative offset, but still comfortably fits on a patient's teeth, particularly where the patient's teeth have a gap in the interproximal region between two teeth that are angled towards each other.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be X, Y, or Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the figures. It should be noted that the orientation of various elements may differ according to other exemplary embodiments, and that such variations are intended to be encompassed by the present disclosure.

The hardware and data processing components used to implement the various processes, operations, illustrative logics, logical blocks, modules, and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, flash memory, hard disk storage) for storing data and/or computer code for completing or facilitating the various processes, layers and circuits described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the systems and methods shown in the various exemplary embodiments are illustrative only. Additionally, any element disclosed in one embodiment may be incorporated or utilized with any other embodiment disclosed herein.

What is claimed is:

1. A method of cutting a dental aligner, the method comprising:
   identifying a first point and a second point based on a first line around tooth (LAT) for a first tooth of a model representative of a dentition of a user, wherein the first point is disposed on a tooth-gingiva interface of the first tooth;
   defining a first cut plane at a distance from the first point toward the second point, the first cut plane intersecting a first line between the first point and the second point;
   identifying a first plurality of points on the first LAT based on the first cut plane;
   identifying a third point and a fourth point corresponding to a second LAT for a second tooth, wherein the third point is disposed on a tooth-gingiva interface of the second tooth;
   defining a second cut plane at a distance from the third point toward the fourth point, the second cut plane intersecting a second line between the third point and the fourth point;
   identifying a second plurality of points on the second LAT for the second tooth based on the second cut plane;
   defining a cut line based on the first plurality of points on the first LAT and the first point and based on the second plurality of points on the second LAT and the third point; and
   controlling a cutting system to cut the dental aligner along the cut line.

2. The method of claim 1, wherein defining the cut line comprises connecting one point from the first plurality of points on the first LAT of the first tooth with one point from the second plurality of points on the second LAT for the second tooth with a straight line.

3. The method of claim 2, wherein the straight line crosses an interproximal surface between the first tooth and the second tooth.

4. The method of claim 3, further comprising generating an interproximal virtual filler between the first tooth and the second tooth, wherein the interproximal surface is located along the interproximal virtual filler between the first tooth and the second tooth.

5. The method of claim 1, further comprising determining an offset value for offsetting the cut line from the first LAT.

6. The method of claim 5, wherein the offset value is based on a predetermined value.

7. The method of claim 1, further comprising defining a cut plane for each of a labial and a lingual side of most teeth in the model.

8. A method of cutting a dental aligner, the method comprising:
   identifying a first point and a second point based on a line around tooth (LAT) for a tooth of a model representative of a dentition of a user, wherein the first point is disposed on a tooth-gingiva interface of the tooth;
   defining a cut plane at a distance from the first point toward the second point, the cut plane intersecting a line between the first point and the second point, wherein the cut plane is perpendicular to the line between the first point and the second point;
   identifying a plurality of points on the LAT based on the cut plane;
   defining a cut line based on the plurality of points on the LAT and the first point and controlling a cutting system to cut the dental aligner along the cut line.

9. A system for cutting a dental aligner, the system comprising:
   a cut line system configured to:
      identify a first point and a second point based on a first line around tooth (LAT) for a first tooth of a model representative of a dentition of a user, wherein the first point is disposed on a tooth-gingiva interface of the first tooth;
      define a first cut plane at a distance from the first point toward the second point, the first cut plane intersecting a first line between the first point and the second point;
      identify a first plurality of points on the first LAT based on the first cut plane;
      identify a third point and a fourth point corresponding to a second LAT for a second tooth, wherein the third point is disposed on a tooth-gingiva interface of the second tooth;
      define a second cut plane at a distance from the third point toward the fourth point, the second cut plane intersecting a second line between the third point and the fourth point;
      identify a second plurality of points on the second LAT for the second tooth based on the second cut plane; and
      define a cut line based on the first plurality of points on the first LAT and the first point and based on the second plurality of points on the second LAT and the third point; and
   a cutting system including a cutting tool configured to cut the dental aligner along the cut line.

10. The system of claim 9, wherein defining the cut line comprises connecting one point from the first plurality of points on the first LAT of the first tooth with one point from the second plurality of points on the second LAT for the second tooth with a straight line.

11. The system of claim 10, wherein the straight line crosses an interproximal surface between the first tooth and the second tooth.

12. The system of claim 11, wherein the cut line system is further configured to generate an interproximal virtual filler between the first tooth and the second tooth, and wherein the interproximal surface is located along the interproximal virtual filler between the first tooth and the second tooth.

13. The system of claim 9, wherein the cut line system is further configured to determine an offset value for offsetting the cut line from the first LAT.

14. The system of claim 13, wherein the offset value is based on a predetermined value.

15. The system of claim 9, wherein the cut line system is configured to define a cut plane for each of a labial and a lingual side of most teeth in the model.

16. A non-transitory computer readable medium storing instructions that, when executed by a processor, cause the processor to perform operations, the operations comprising:

identifying a first point and a second point based on a first line around tooth (LAT) for a first tooth of a model representative of a dentition of a user;

defining a first cut plane at a distance from the first point toward the second point, the first cut plane intersecting a first line between the first point and the second point;

identifying a first plurality of points on the first LAT based on the first cut plane;

identifying a third point and a fourth point corresponding to a second LAT for a second tooth;

defining a second cut plane at a distance from the third point toward the fourth point, the second cut plane intersecting a second line between the third point and the fourth point;

identifying a second plurality of points on the second LAT for the second tooth based on the second cut plane; and defining a cut line for cutting a dental aligner based on the first plurality of points on the first LAT and the first point and based on the second plurality of points on the second LAT and the third point.

17. The non-transitory computer readable medium of claim 16, wherein the first point is disposed on a tooth-gingiva interface of the tooth.

18. A non-transitory computer readable medium storing instructions that, when executed by a processor, cause the processor to perform operations, the operations comprising:

identifying a first point and a second point based on a line around tooth (LAT) for a tooth of a model representative of a dentition of a user;

defining a cut plane at a distance from the first point toward the second point, the cut plane intersecting a line between the first point and the second point, wherein the cut plane is perpendicular to the line between the first point and the second point;

identifying a plurality of points on the LAT based on the cut plane, wherein the plurality of points on the LAT are identified based on where the cut plane meets the LAT; and defining a cut line for cutting a dental aligner based on the plurality of points on the LAT and the first point.

* * * * *